US012324681B2

(12) United States Patent
Kim et al.

(10) Patent No.: US 12,324,681 B2
(45) Date of Patent: Jun. 10, 2025

(54) ELECTRONIC DEVICE AND METHOD OF MEASURING BIOMETRIC INFORMATION USING SAME

(71) Applicant: Samsung Display Co., Ltd., Yongin-Si (KR)

(72) Inventors: Yuna Kim, Seoul (KR); Soojung Lee, Suwon-si (KR); Seungwook Chun, Daegu (KR); Boram Choi, Asan-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 196 days.

(21) Appl. No.: 17/944,219

(22) Filed: Sep. 14, 2022

(65) Prior Publication Data
US 2023/0096622 A1    Mar. 30, 2023

(30) Foreign Application Priority Data

Sep. 28, 2021  (KR) .......................... 10-2021-0127636

(51) Int. Cl.
*A61B 5/00*   (2006.01)
*H10K 65/00*  (2023.01)

(52) U.S. Cl.
CPC ............ *A61B 5/445* (2013.01); *A61B 5/0082* (2013.01); *A61B 5/441* (2013.01); *A61B 5/4842* (2013.01);
(Continued)

(58) Field of Classification Search
CPC ....... A61B 5/445; A61B 5/0082; A61B 5/441; A61B 5/4842; A61B 5/6898; A61B 5/742;
(Continued)

(56) References Cited

U.S. PATENT DOCUMENTS 11,074,862 B2   7/2021  Bae et al.
11,196,969 B2 * 12/2021 Ong ..................... G09G 3/2003
(Continued)

FOREIGN PATENT DOCUMENTS

JP       2021-039342 A    3/2021
KR    10-2017-0037738 A    4/2017
(Continued)

OTHER PUBLICATIONS

Patwardhan, Sachin V., et al. "Measuring acne using Coproporphyrin III, Protoporphyrin IX, and lesion-specific inflammation: an exploratory study." Archives of dermatological research 309 (2017): 159-167. (Year: 2017).*
(Continued)

*Primary Examiner* — Sean D Mattson
(74) *Attorney, Agent, or Firm* — Innovation Counsel LLP

(57) ABSTRACT

An electronic device includes a display panel and a biometric information module. The display panel includes red-light emitting elements, green-light emitting elements, blue-light emitting elements, and light receiving elements that are spaced from each other. The blue-light emitting elements emit blue light in a biometric information mode of the electronic device. The light receiving elements receive at least one of red light and green light in the biometric information mode of the electronic device after the blue-light emitting elements have emitted the blue light. The light receiving elements generate electrical signals in response to the at least one of the red light and the green light. The biometric information module is electrically connected to the display panel and generates biometric information about a skin of a user based on the electrical signals.

23 Claims, 16 Drawing Sheets

(52) U.S. Cl.
CPC ............ A61B 5/6898 (2013.01); A61B 5/742 (2013.01); H10K 65/00 (2023.02)

(58) Field of Classification Search
CPC ..... A61B 5/0075; A61B 5/0077; A61B 5/444; A61B 5/0013; A61B 5/4836; A61B 5/7465; G06V 10/141; G06V 10/143; G06V 10/17; G06V 40/168; H10K 65/00; H10K 59/13; H10K 59/121; H10K 39/34
See application file for complete search history.

(56) References Cited

U.S. PATENT DOCUMENTS

| | | | | |
|---|---|---|---|---|
| 2003/0086703 A1* | 5/2003 | Kollias | ................. | G03B 15/00 396/14 |
| 2005/0104507 A1* | 5/2005 | Huiberts | ............ | H04N 1/00129 313/500 |
| 2009/0137908 A1* | 5/2009 | Patwardhan | ........... | A61B 5/444 600/476 |
| 2011/0002510 A1* | 1/2011 | Hanna | ................. | G06V 10/141 382/117 |
| 2015/0039061 A1* | 2/2015 | Hong | ................... | A61N 5/0616 607/90 |
| 2017/0337413 A1* | 11/2017 | Bhat | .................. | G06V 40/1347 |
| 2018/0106676 A1* | 4/2018 | Jang | ...................... | A61B 5/6898 |
| 2021/0066669 A1* | 3/2021 | Kubota | ................ | H10K 59/121 |
| 2022/0293682 A1* | 9/2022 | Einzinger | .............. | H10K 30/30 |

FOREIGN PATENT DOCUMENTS

| | | |
|---|---|---|
| KR | 10-2180920 B1 | 11/2020 |
| KR | 10-2021-0024274 A | 3/2021 |

OTHER PUBLICATIONS

Alec B. Walter, et al.; "Optimization of optical parameters for improved photodynamic therapy of *Staphylococcus aureus* using endogenous coproporphyrin III"; Photodiagnosis and Photodynamic Therapy 29 (2020) 101624; 2020; pp. 1-9; Elsevier B.V.

Sachin V. Patwardhan, et al.; "Measuring acne using Coproporphyrin III, Protoporphyrin IX, and lesion-specific inflammation"; Arch Dermatol Res (2017) 309; Feb. 8, 2017; pp. 159-167, Springer Nature.

* cited by examiner

ELECTRONIC DEVICE AND METHOD OF MEASURING BIOMETRIC INFORMATION USING SAME

CROSS-REFERENCE TO RELATED APPLICATIONS

This application claims priority under 35 U.S.C. § 119 to Korean Patent Application No. 10-2021-0127636 filed on Sep. 28, 2021 in the Korean Intellectual Property Office; the Korean Patent Application is incorporated by reference.

BACKGROUND

The technical field relates to an electronic device and a method of using the electronic device to measure biometric information, such as skin condition information.

Electronic devices may be portable and may perform various functions. A portable electronic device may include a display device for displaying images and information.

SUMMARY

Embodiments may be related to an electronic device capable of measuring biometric information of a user using a light emitting element and a light receiving element included in a display panel of the electronic device without requiring additional parts for measuring the biometric information. Embodiments may be related to a method of using the electronic device to measure biometric information.

Embodiments may be related to an electronic device capable of selectively receiving red light and green light reflected from an inflammation of a user's skin and diagnosing the user's skin condition based on the received light. Embodiments may be related to a method of using the electronic device to measure biometric information.

According to an embodiment, an electronic device includes a display panel including a plurality of unit pixels, each of the unit pixels having a light emitting element emitting red light, green light, or blue light and a light receiving element, which is positioned adjacent to the light emitting element and which receives reflection light reflected from a skin of a user and a biometric information measurement module electrically connected to the display panel and generating biometric information about the skin of the user based on the reflection light. When a biometric information measurement mode is activated, the light emitting element selectively emits the blue light. When the blue light is reflected from the skin of the user, the light receiving element selectively receives red light or green light among the reflected reflection light. The biometric information measurement module generates a skin condition image of the user based on a reflection location and a light receiving amount of the received red light or the received green light and generates skin condition information of the user based on the generated skin condition image.

The biometric information measurement module may determine that the biometric information is in a first inflammation state, when the light receiving element receives the green light, and may determine that the biometric information is in a second inflammation state, when the light receiving element receives the red light.

In the biometric information measurement mode, the biometric information measurement module may allow a blue light emitting element to emit light in a high power mode.

According to an embodiment, an electronic device includes a display panel including a plurality of unit pixels, each of the unit pixels having a light emitting element emitting red light, green light, or blue light and a light receiving element, which is positioned adjacent to the light emitting element and which receives reflection light reflected from a skin of a user and a biometric information measurement module electrically connected to the display panel and generating biometric information about the skin of the user based on the reflection light. A display area in which a first area and a second area adjacent to the first area are separated is defined in the display panel. An emission area of the blue light for each of the unit pixels in the second area is greater than an emission area of the blue light for each of the unit pixels in the first area.

The display panel may further include a base layer and a pixel defining layer, which is disposed on the base layer and on which an opening is defined. The light emitting element and the light receiving element may be separated by the pixel defining layer.

The light emitting element may include a first electrode, a second electrode, and a light emitting layer, which is interposed between the first electrode and the second electrode and which emits the red light, the green light, or the blue light. The first electrode and the second electrode may face each other.

The light receiving element may include a first electrode, a second electrode, and a light receiving layer, which is interposed between the first electrode and the second electrode and which converts incident light into an electrical signal. The first electrode and the second electrode may face each other.

A plurality of blue light emitting areas, in each of which the blue light emits, may be defined in the display area. The number of the plurality of blue light emitting areas for each of the unit pixels disposed in the second area may be greater than the number of the plurality of blue light emitting areas for each of the unit pixels disposed in the first area.

The light emitting element disposed in the first area may include a blue light emitting element, a red light emitting element, and a green light emitting element. The light emitting element disposed in the second area may include only a blue light emitting element.

The light receiving element may selectively receive red light and green light among the reflection light.

The biometric information measurement module may determine that the biometric information is in a first inflammation state, when the light receiving element receives the green light, and may determine that the biometric information is in a second inflammation state, when the light receiving element receives the red light.

The biometric information measurement module may generate biometric information about the skin of the user based on a reflection location and a light receiving amount of the reflection light.

The biometric information measurement module may include a light emitting part selectively emitting the blue light through the light emitting element in a biometric information measurement mode, a light receiving part receiving the reflection light through the light receiving element and obtaining information about a reflection location and a light receiving amount of the reflection light, and a diagnosis part measuring the biometric information including inflammation information about the skin of the user based on the information about the reflection location and the light receiving amount of the reflection light.

The inflammation information may include a location of an inflammation in the skin of the user, which is generated based on the reflection location of the reflection light, and a degree of the inflammation in the skin of the user, which is generated based on the light receiving amount of the reflection light. The diagnosis part may diagnose a condition of the skin of the user based on the inflammation information.

A non-display area surrounding the display area may be further defined in the display panel. The second area on a plane may be defined between the first area and the non-display area.

In a biometric information measurement mode, the biometric information measurement module may allow the blue light emitting element in the second area to selectively emit light in a high power mode.

According to an embodiment, a method of measuring biometric information includes selectively emitting blue light in a display panel when a biometric information measurement mode is activated, selectively receiving red light or green light among the reflected reflection light when the blue light is reflected from a skin of a user, generating a skin condition image of the user based on a reflection location and a light receiving amount of the received red light or the received green light, and generating skin condition information of the user based on the generated skin condition image.

A light emitting element of the display panel may emit the red light, green light, and the blue light. The method of measuring biometric information may further include selectively emitting the blue light in a high power mode when the biometric information measurement mode is activated.

A display area, which includes a blue light emitting area emitting the blue light, a red light emitting area emitting the red light, and a green light emitting area emitting the green light, and a non-display area adjacent to the display area may be defined in the display panel. The number of the blue light emitting area may be greater than the number of the red light emitting area or the green light emitting area.

The display area may include a first area including the red light emitting area, the green light emitting area, and the blue light emitting area and a second area including only the blue light emitting area. In the biometric information measurement mode, the blue light emitting area of the second area may emit light in a high power mode.

The blue light may be reflected to a first inflammation of the skin of the user and received as the green light. The blue light may be reflected to a second inflammation and received as the red light.

The skin condition information of the user may include a location and degree of each of the first inflammation and the second inflammation, which are present in the skin of the user.

The method of measuring biometric information may further include diagnosing a skin condition based on the skin condition information of the user and determining a customized prescription based on the diagnosed skin condition.

An embodiment may be related to an electronic device. The electronic device may include a display panel and a biometric information module. The display panel may include red-light emitting elements, green-light emitting elements, blue-light emitting elements, and light receiving elements that are spaced from each other. The blue-light emitting elements may emit blue light in a biometric information mode of the electronic device. The light receiving elements may receive at least one of red light and green light in the biometric information mode of the electronic device after the blue-light emitting elements have emitted the blue light. The light receiving elements may generate electrical signals in response to the at least one of the red light and the green light. The biometric information module may be electrically connected to the display panel and may generate biometric information about a skin of a user based on the electrical signals.

The biometric information module may determine an inflammation state of a location of the skin of the user based on whether light reflected from the location of the skin of the user is red or green.

The blue-light emitting elements may emit a first amount of light in the biometric information mode of the electronic device. The blue-light emitting elements may emit a second amount of light to display a blue component of an image in an image display mode of the electronic device. The first amount of light may be greater than the second amount of light.

An embodiment may be related to an electronic device. The electronic device may include a display panel and a biometric information module. The display panel may include a first edge, a second edge, red-light emitting elements, green-light emitting elements, blue-light emitting elements, and light receiving elements that are spaced from each other. The first edge and the second edge may be opposite each other. The blue-light emitting elements may emit blue light in a biometric information mode of the electronic device. The light receiving elements may receive reflected light in the biometric information mode of the electronic device after the blue-light emitting elements have emitted the blue light. The light receiving elements may generate electrical signals in response to the reflected light. The light receiving elements may include a first light receiving element and a second light receiving element. The first light receiving element may be closer to the first edge than the second light receiving element is to the first edge, may be farther from the first edge than the second light receiving element is from the second edge, and may be farther from the second edge than the second light receiving element is from the second edge. The first light receiving element may neighbor one of the red-light emitting elements with no intervening blue-light emitting element between the first light receiving element and the one of the red-light emitting elements. The second light receiving element may neighbor two of the blue-light emitting elements with no intervening red-light emitting element or intervening green-light emitting element between the second light receiving element and either of the two of the blue-light emitting elements. The biometric information module may be electrically connected to the display panel and may generate biometric information about a skin of the user based on the electrical signals.

The display panel may include a base layer and a pixel defining layer. The pixel defining layer may overlap the base layer and may include openings that correspond to the red-light emitting elements, the green-light emitting elements, the blue-light emitting elements, and the light receiving elements.

The second light receiving element may neighbor three of the blue-light emitting elements with no intervening red-light emitting element or intervening green-light emitting element between the second light receiving element and any of the three of the blue-light emitting elements.

The second light receiving element may include a first electrode, a second electrode, and a light receiving layer. The light receiving layer may be interposed between the first electrode and the second electrode and may convert incident light into an electrical signal. The first electrode and the second electrode may overlap each other.

The first light receiving element may neighbor one of the green-light emitting elements with no intervening blue-light emitting element between the first light receiving element and the one of the green-light emitting elements.

The second light receiving element may neighbor four of the blue-light emitting elements with no intervening red-light emitting element or intervening green-light emitting element between the second light receiving element and any of the four of the blue-light emitting elements.

The light receiving elements may generate the electrical signals in response to at least one of red light and green light in the reflected light.

The biometric information module may determine an inflammation state of a location of the skin of the user based on whether light reflected from the location of the skin of the user is red or green.

The biometric information module may generate the biometric information about the skin of the user based on at least one of a reflection location and a received amount of the reflected light.

The biometric information module may include a diagnosis part. The diagnosis part may determine inflammation information about the skin of the user based on the electrical signals.

The inflammation information may include inflammation location information and inflammation degree information. The diagnosis part may determine the inflammation location information based on a reflection location of the reflected light. The diagnosis part may determine the inflammation degree information based on a received amount of the reflected light.

The display panel may include a non-display area surrounding the red-light emitting elements, the green-light emitting elements, the blue-light emitting elements, and the light receiving elements. The second light receiving element may be closer to the non-display area than the first light receiving element is to the non-display area.

The two of the blue-light emitting elements may emit a first amount of light in a biometric information mode of the electronic device. The two of the blue-light emitting elements may emit a second amount of light in an image display mode of the electronic device. The first amount of light may be greater than the second amount of light.

An embodiment may be related to a method for measuring biometric information. The method may include the following steps: emitting, using a display panel, blue light toward a skin of a user; receiving, using the display panel, at least one of red light and green light reflected from the skin of the user; and generating skin condition information of the user based on at least one of a reflection location and a received amount of the at least one of the red light and the green light.

The display panel may emit a first amount of blue light when the user does not directly look at a display area of the display panel. The display panel may emit a second amount of blue light when the user directly looks at an image displayed in the display area of the display panel. The first amount of blue light may be greater than the second amount of blue light.

The display panel may include more blue-light emitting elements than red-light emitting elements or green-light emitting elements.

The display panel may include a first edge, a second edge, red-light emitting elements, green-light emitting elements, blue-light emitting elements, and light receiving elements that are spaced from each other. The first edge and the second edge may be opposite each other. The light receiving elements may include a first light receiving element and a second light receiving element. The first light receiving element may be closer to the first edge than the second light receiving element is to the first edge, may be farther from the first edge than the second light receiving element is from the second edge, and may be farther from the second edge than the second light receiving element is from the second edge. The first light receiving element may neighbor one of the red-light emitting elements with no intervening blue-light emitting element between the first light receiving element and the one of the red-light emitting elements. The second light receiving element may neighbor two of the blue-light emitting elements with no intervening red-light emitting element or intervening green-light emitting element between the second light receiving element and either of the two of the blue-light emitting elements.

The display panel may receive the red light reflected from a first inflammation of the skin of the user. The display panel may receive the green light reflected from a second inflammation of the skin of the user.

The method may include the following step: displaying, using the display panel, the skin condition information of the user to the user. The skin condition information of the user may include at least one of a location and a degree of each of the first inflammation and the second inflammation.

The method may include the following step: determining, using a module electrically connected to the display panel, a prescription based on the skin condition information of the user.

DETAILED DESCRIPTION

Figure 1:
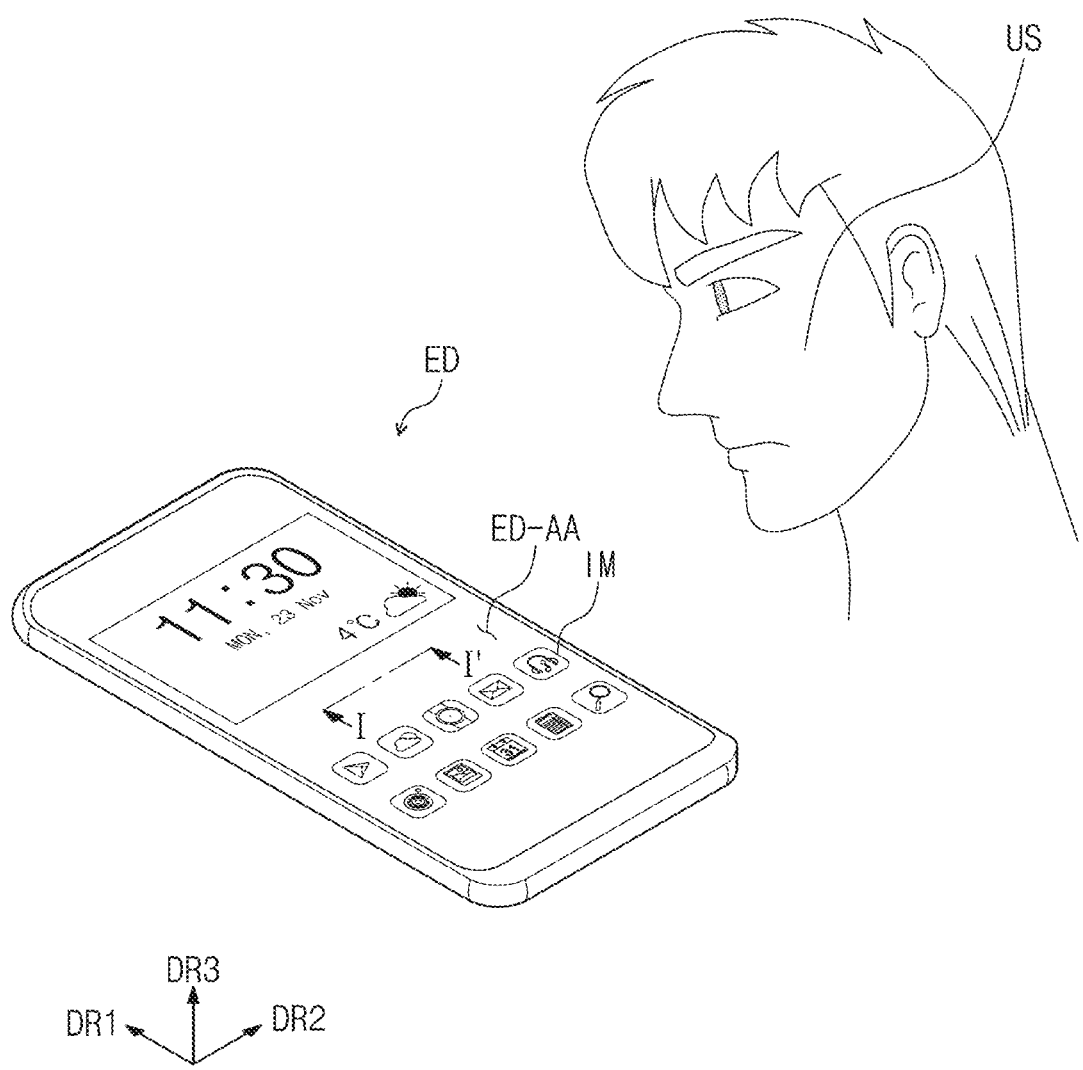
FIG. 1 is a perspective view of an electronic device according to an embodiment.

Examples of embodiments are described with reference to the accompanying drawings.

In the description and the drawings, the same reference numerals may refer to the same components or similar elements. In drawings, dimensions may be exaggerated for clarity.

Although the terms "first," "second," etc. may be used to describe various elements, the elements should not be limited by the terms. The terms may be used to distinguish one element from another element. A first element may be referred to as a second element, and similarly a second element may be referred to as a first element. The description of an element as a "first" element may not require or imply the presence of a second element or other elements. The terms "first," "second," etc. may be used to differentiate different categories or sets of elements. For conciseness, the terms "first," "second," etc. may represent "first-category (or first-set)," "second-category (or second-set)," etc., respectively.

The terms "include," "comprise," "have," etc. may specify the presence of elements and may not preclude the presence or addition of one or more other elements.

The term "connect" may mean "directly connect" or "indirectly connect." The term "connect" may mean "mechanically connect" and/or "electrically connect." The term "connected" may mean "electrically connected" or "electrically connected through no intervening transistor." The term "insulate" may mean "electrically insulate" or "electrically isolate." The term "conductive" may mean "electrically conductive." The term "drive" may mean "operate" or "control." The term "include" may mean "be made of." The term "adjacent" may mean "immediately adjacent." The expression that an element extends in a particular direction may mean that the element extends lengthwise in the particular direction and/or that the lengthwise direction of the element is in the particular direction. The term "correspond to" may mean "be." The term "measurement" may mean "assessment" or "determination."

Figure 2A:
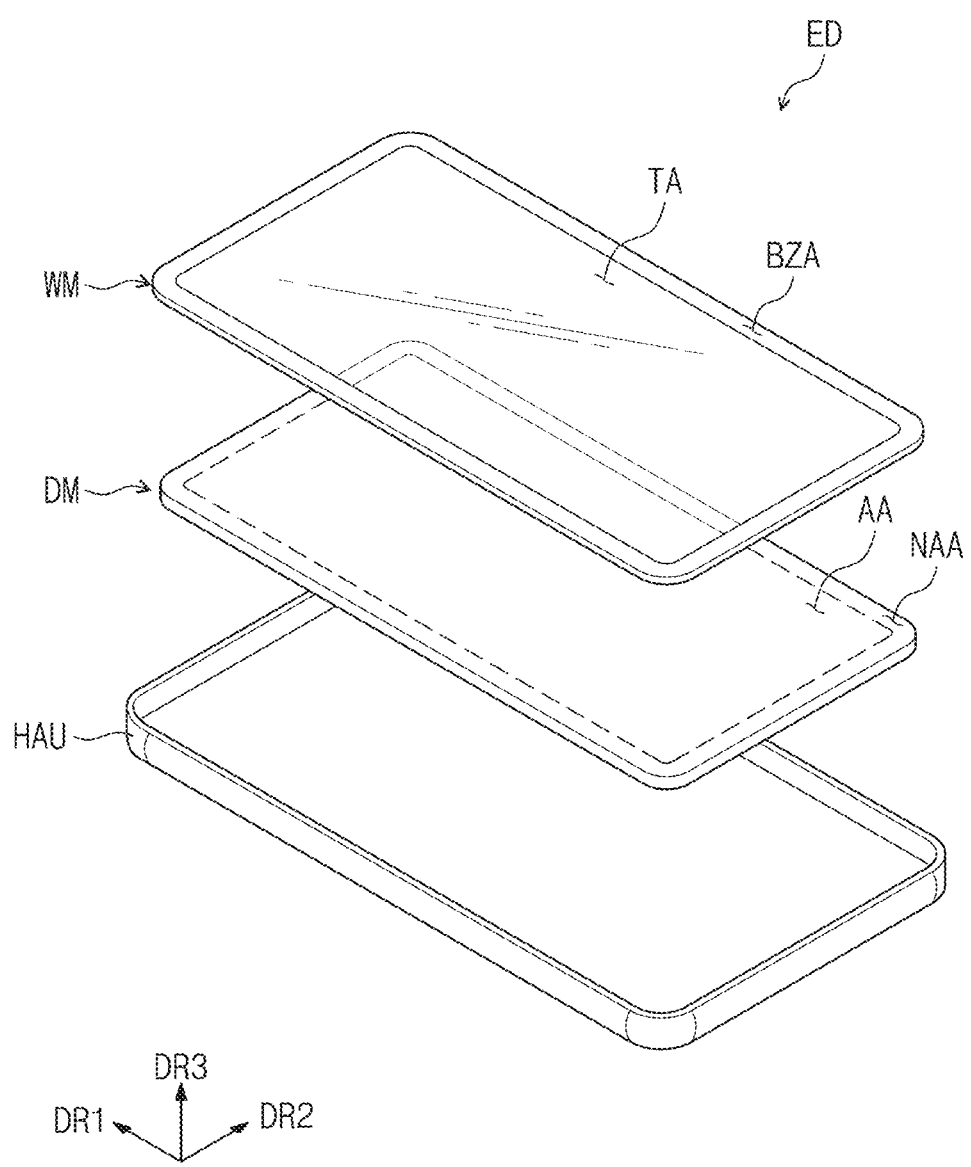
FIG. 2A is an exploded perspective view of an electronic device according to an embodiment.
Figure 2B:
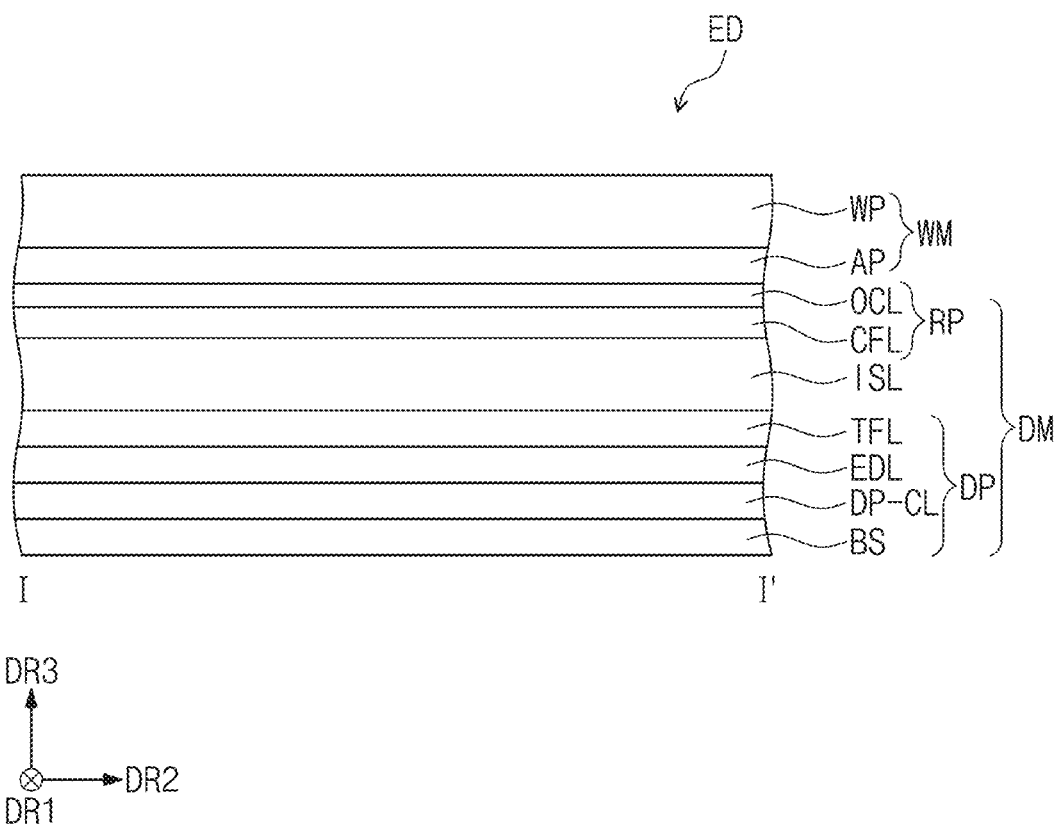
FIG. 2B is a cross-sectional view illustrating a portion corresponding to a line I-I' of FIG. 1 according to an embodiment.

FIG. 1 is a perspective view of an electronic device ED according to an embodiment. FIG. 2A is an exploded perspective view of an electronic device ED according to an embodiment. FIG. 2B is a cross-sectional view illustrating a portion corresponding to a line I-I' of FIG. 1 according to an embodiment.

The electronic device ED shown in FIGS. 1 to 2B may operate depending on electrical signals. For example, the electronic device ED may be a mobile phone, a tablet PC, a car navigation system, a game console, or a wearable device. FIG. 1 illustrates that the electronic device ED is a mobile phone.

The electronic device ED may display an image IM through/in a display area ED-AA. The display area ED-AA may include a flat face positioned in a plane defined by a first direction axis DR1 and a second direction axis DR2. The display area ED-AA may further include a curved surface that is bent from at least one side of the flat face. The display area ED-AA may include only the flat face. The display area ED-AA may include two or more (e.g., four) curved surfaces respectively bent from four side surfaces of the flat face.

FIG. 1 and the following drawings illustrate first to fourth direction axes DR1 to DR4. Directions indicated by the first to fourth direction axes DR1, DR2, DR3, and DR4 described in this specification may be illustrative and may be converted into other directions. The directions indicated by the first to fourth direction axes DR1, DR2, DR3, and DR4 may be described as first to fourth directions.

In this specification, the first direction axis DR1 and the second direction axis DR2 may be perpendicular to each other. The third direction axis DR3 may indicate a direction normal/perpendicular to the plane defined by the first direction axis DR1 and the second direction axis DR2. The fourth direction axis DR4 may indicate a direction between the first direction axis DR1 and the second direction axis DR2.

A thickness direction of the electronic device ED may be parallel to and/or consistent with the third direction axis DR3. In this specification, front surfaces (or top surfaces) and rear surfaces (or bottom surfaces) may be defined based on the third direction axis DR3.

The image IM provided by the electronic device ED may include a still image and/or a moving image. In FIG. 1, a clock window and icons are illustrated as an example of the image IM. A surface on/through which the image IM is displayed may correspond to a front surface of the electronic device ED and may correspond to a front surface of a window member WM.

The electronic device ED may detect a user input. The user input may be related to a portion of the user's body, light, heat, pressure, or the like. The electronic device ED may detect a user input through the display area ED-AA and may react to the detected input signal.

The electronic device ED may detect biometric information applied from a skin US of the user's face. The electronic device ED may emit blue light to the skin US of the user's face, may receive red light or green light reflected from the skin US, and may measure biometric information based on the reflected light. The electronic device ED may generate information about an inflammation in the user's skin US using the reflected light reflected from the skin US.

The electronic device ED may detect the user input applied to the side surface or rear surface of the electronic device ED depending on a design of the electronic device ED.

The electronic device ED may detect biometric information such as a fingerprint. A fingerprint recognition area may be provided in the display area ED-AA of the electronic device ED. The fingerprint recognition area may be provided in all areas of the display area ED-AA or may be provided in some areas of the display area ED-AA.

Referring to FIGS. 2A and 2B, the electronic device ED may include a display module DM, the window member WM, and housing HAU. The window member WM may be coupled to the housing HAU to enclose the display module DM.

The display module DM may include a display element layer EDL, a color filter layer CFL, and an organic planarization layer OCL. The organic planarization layer OCL may be disposed on the color filter layer CFL and may include an infrared absorber.

The display module DM may include a display area AA and a non-display area NAA. The display area AA may display images according to electrical signals. The display area AA may detect an external input.

The non-display area NAA may be positioned adjacent to at least one side of the display area AA. The non-display area NAA may surround the display area AA. Some portions of the non-display area NAA may be optional. A driving circuit or driving wires for driving the display area AA may be positioned in the non-display area NAA.

The display module DM may include a display panel DP and an anti-reflection member RP. The display module DM may include an input sensing layer ISL disposed between the display panel DP and the anti-reflection member RP.

The display panel DP may include a base layer BS, a circuit layer DP-CL disposed on the base layer BS, the display element layer EDL disposed on the circuit layer DP-CL, and an encapsulation layer TFL disposed on the display element layer EDL. The encapsulation layer TFL may cover the display element layer EDL.

The window member WM may be disposed on the display module DM. The window member WM may include a window WP and an adhesive layer AP. The adhesive layer AP may be interposed between the anti-reflection member RP and the window WP. The adhesive layer AP may be an optically clear adhesive film (OCA) or an optically clear adhesive resin layer (OCR). The adhesive layer AP may be optional.

The window WP may cover a front/upper face of the display module DM. The window WP may have a shape corresponding to the shape of the display module DM. The window WP may include an optically transparent insulating material. The window WP may be a glass substrate or a polymer substrate. The window WP may be a tempered glass substrate. The window WP may correspond to a top layer of the electronic device ED.

The window member WM may include a transmissive part TA and a bezel part BZA. The transmissive part TA may overlap the display area AA of the display module DM. The bezel part BZA may overlap the non-display area NAA of the display module DM.

The front surface of the window member WM corresponds to the front surface of the electronic device ED. The user may visually perceive an image provided through the transmissive part TA.

The bezel part BZA may define the shape of the transmissive part TA. The bezel part BZA may surround the transmissive part TA. The bezel part BZA may be positioned adjacent to only one, two, or three sides of the transmissive part TA. A part of the bezel part BZA may be optional.

A part of the electronic device ED visible through the bezel part BZA may have a relatively low light transmittance compared to a part visible through the transmissive part TA. The bezel part BZA may have a predetermined color.

The anti-reflection member RP may include the color filter layer CFL, and the organic planarization layer OCL. The anti-reflection member RP may block reflected light, may reduce the reflectance of external light, and/or may absorb a part of light incident from the outside.

The input sensing layer ISL may be disposed on the display panel DP. The input sensing layer ISL may detect an external input applied from the outside. The external input may be a user input. The user input may be related to a part of a user body, light, heat, a pen, or pressure.

Figure 3:
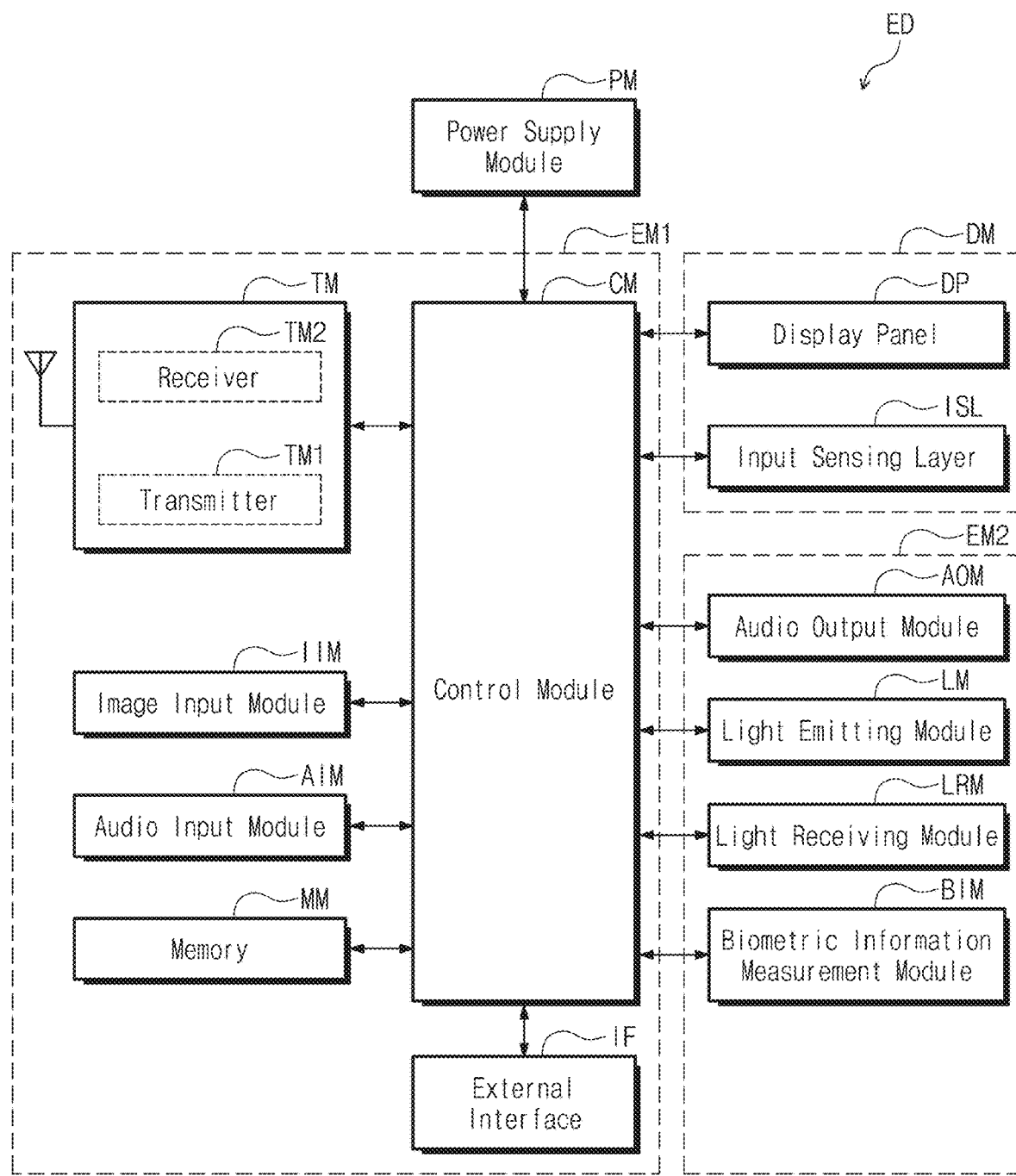
FIG. 3 is a block diagram of an electronic device according to an embodiment.

FIG. 3 is a block diagram of an electronic device according to an embodiment.

Referring to FIG. 3, the electronic device ED may include the display module DM, a power supply module PM, a first electronic module EM1, and a second electronic module EM2. The display module DM, the power supply module PM, the first electronic module EM1, and the second electronic module EM2 may be electrically connected to one another.

The power supply module PM supplies a power necessary for the overall operation of the electronic device ED. The power supply module PM may include a battery module.

Each of the first electronic module EM1 and the second electronic module EM2 may include functional modules for operating the electronic device ED.

The first electronic module EM1 may be directly mounted on a motherboard electrically connected to the display module DM or may be mounted on a separate board and electrically connected to the motherboard through a connector (not illustrated).

The first electronic module EM1 may include a control module CM, a wireless communication module TM, an image input module IIM, an audio input module AIM, a memory MM, and an external interface IF. Some of the modules may be electrically connected to the motherboard through a flexible circuit board without being mounted on the motherboard.

The control module CM controls the overall operation of the electronic device ED. The control module CM may be a microprocessor. The control module CM activates or deactivates the display module DM. The control module CM may control other modules such as the image input module IIM, the audio input module AIM, or the like based on a touch signal received from the display module DM. The control module CM may receive pieces of information necessary to detect the user's biometric information from the light emitting element and the light receiving element of the display panel DP and then may deliver the pieces of information to a biometric information measurement module BIM in the second electronic module EM2. The control module CM may receive information about the amount of red light received by a light receiving element of the display panel DP and may deliver the information about the amount of red light to the biometric information measurement module BIM. The biometric information measurement module BIM may generate information about an inflammation in a user's skin based on the information about the amount of red light.

The control module CM may control an emission mode of the pixel PX of the display panel DP. The control module CM may adjust the amount of light emitted by a blue light emitting element that emits blue light in a biometric information measurement mode. The control module CM may execute a high power mode to increase the amount of blue light emitted from the light emitting element of the display panel DP by controlling a light emitting module LM in the biometric information measurement mode.

The wireless communication module TM may transmit/receive wireless signals to/from another terminal using Bluetooth or Wi-Fi. The wireless communication module TM may transmit/receive voice signals using general communication lines. The wireless communication module TM may include a transmitter TM1 that modulates and transmits a transmission signal, and may include a receiver TM2 that demodulates a reception signal.

The image input module IIM processes and converts an image signal into image data to be displayed on the display module DM. The audio input module AIM receives an external sound signal from a microphone in a recording mode, a speech recognition mode, or the like and then converts the external sound signal into electrical voice data.

The external interface IF may be connected to an external charger, a wired/wireless data port, a card socket (e.g., a memory card, a SIM/UIM card, or the like), or the like.

The second electronic module EM2 may include an audio output module AOM, the light emitting module LM, a light receiving module LRM, and the biometric information measurement module BIM. The modules may be mounted directly on a motherboard, may be mounted on a separate board and electrically connected to the display module DM through a connector (not illustrated), and/or may be electrically connected to the first electronic module EM1.

The audio output module AOM converts audio data received from the wireless communication module TM or audio data stored in the memory MM and then outputs the converted data to the outside.

In the biometric information measurement mode, the light emitting module LM may emit blue light by controlling the light emitting element of the display panel DP in response to a signal received from the control module CM.

In the biometric information measurement mode, the light receiving module LRM may receive red light and/or green light by controlling the light receiving element of the display panel DP in response to the signal received from the control module CM.

In the biometric information measurement mode, the biometric information measurement module BIM may generate and/or determine information about the user's skin together with the display panel DP, the light emitting module LM, the light receiving module LRM, and the control module CM. When the biometric information measurement mode is executed by the control module CM depending on a user input, the light emitting module LM may emit blue light through the light emitting element of the display panel DP. Afterward, when the red light and green light reflected from the user's skin US (see FIG. 1) are received by the light receiving module LRM through the light receiving element, the biometric information measurement module BIM may generate and/or determine biometric information about the user's skin based on the received light and may diagnose the status of the user's skin. The biometric information measurement module BIM may determine an acne status of the user's skin through the reflected light that is reflected from acne bacteria in the user's skin US.

Figure 4A:
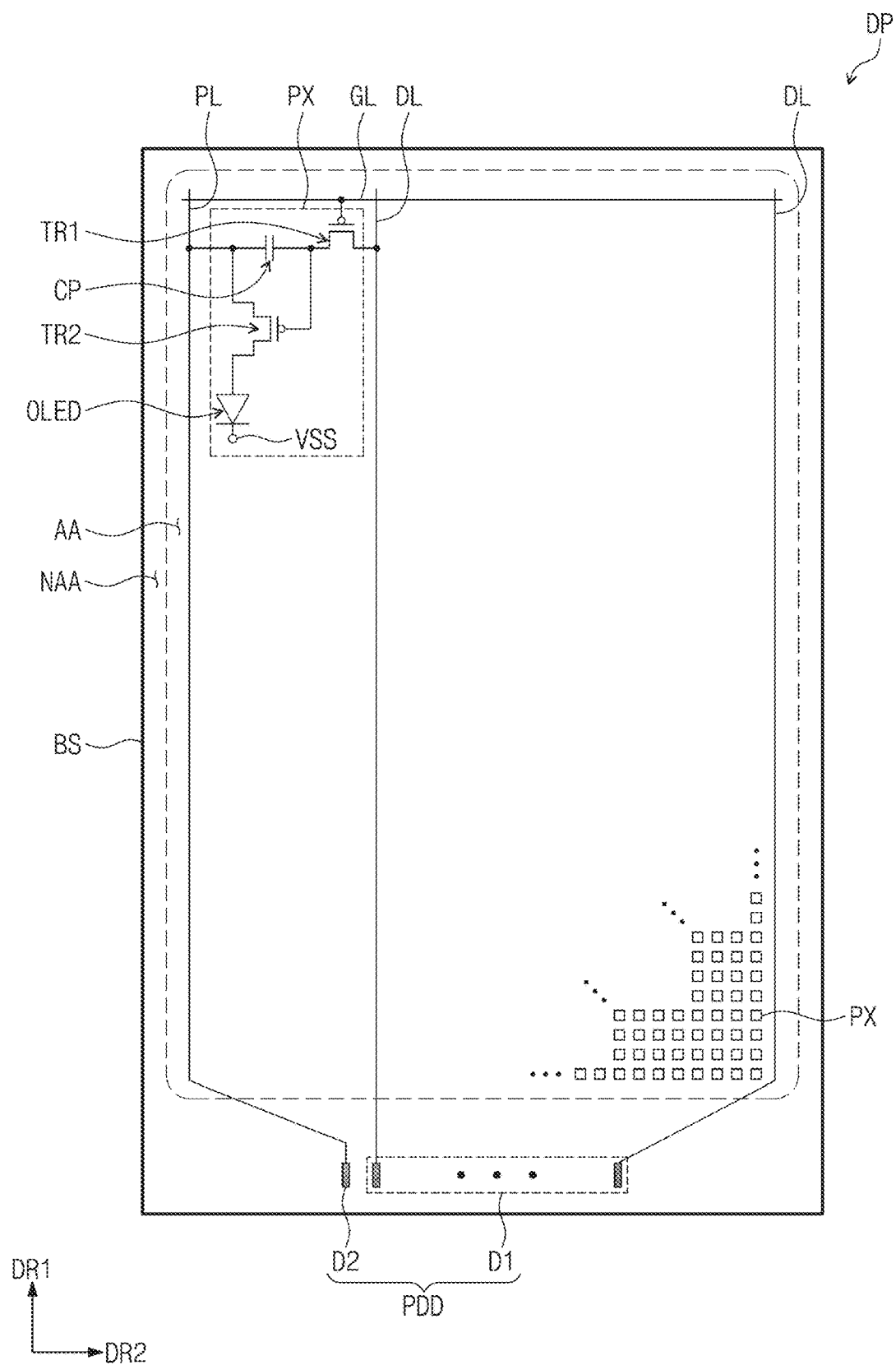
FIG. 4A is a plan view of a display panel according to an embodiment.
Figure 4B:
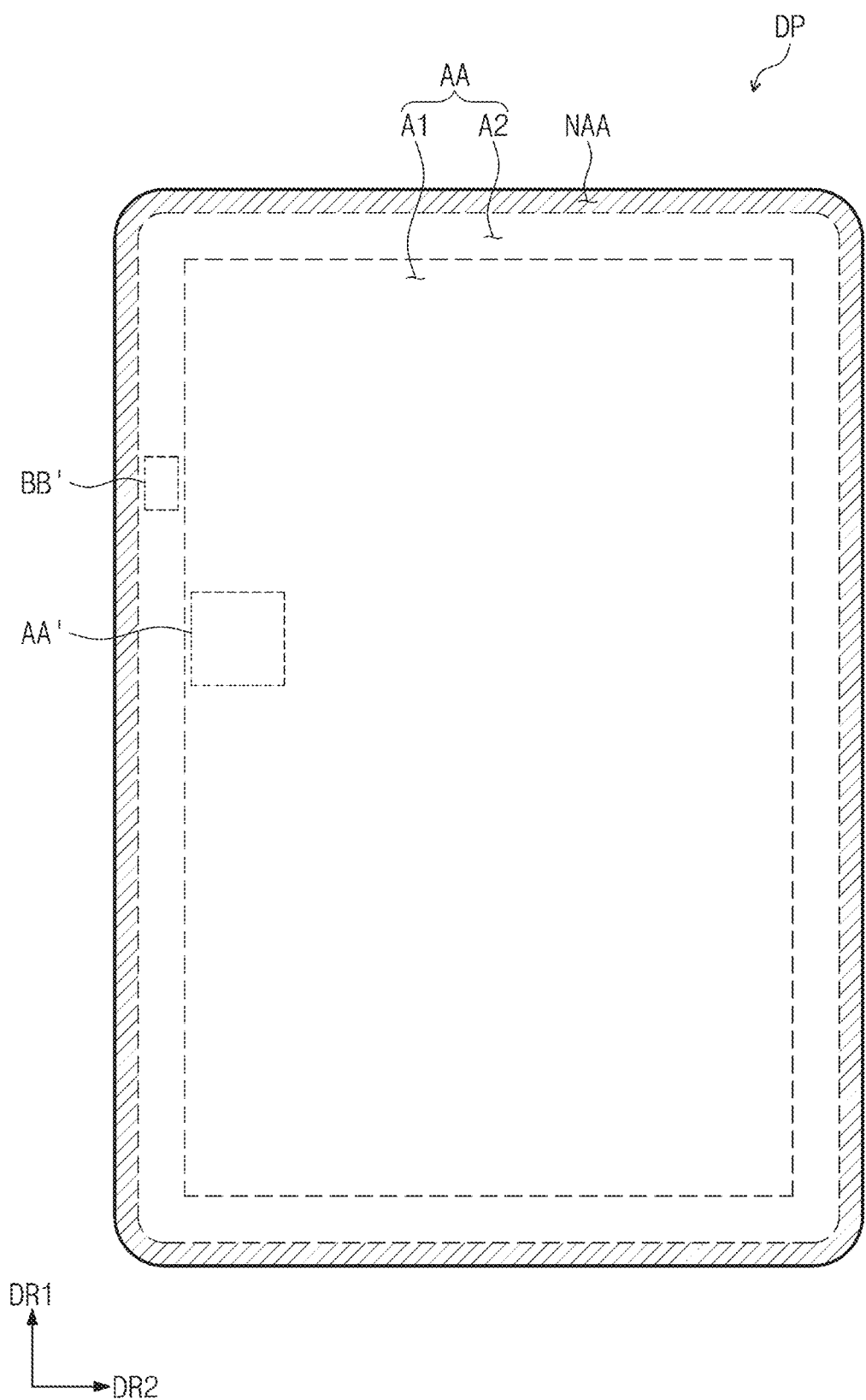
FIG. 4B is a plan view of a display panel according to an embodiment.

FIGS. 4A and 4B are plan views of a display panel according to one or more embodiments Referring to FIG. 4A, the display panel DP may include the base layer BS, a plurality of pixels PX, a plurality of signal wires GL, DL, and PL, and a plurality of display pads PDD.

The display area AA of the display panel DP may display an image in response to input signals. The non-display area NAA may accommodate a driving circuit and/or driving wires. The plurality of pixels PX may be positioned in the display area AA.

The base layer BS may be a stacked structure including a silicon substrate, a plastic substrate, a glass substrate, an insulating film, and/or a plurality of insulating layers.

The plurality of signal wires GL, DL, and PL are connected to the pixels PX so as to deliver electrical signals to the pixels PX. A scan wire GL, a data wire DL, and a power supply wire PL are illustrated as examples. The signal wires may further include at least one of an initialization voltage wire and a light emission control wire.

An equivalent circuit diagram of one pixel PX is illustrated FIG. 4A. The pixel PX may include a first transistor TR1, a capacitor CP, a second transistor TR2, and a light emitting element OLED. The first transistor TR1 may be a switching element to control turn-on and turn-off of the pixel PX. The first transistor TR1 may deliver or block a data signal delivered through the data wire DL in response to a scan signal delivered through the scan wire GL.

The capacitor CP is connected to the first transistor TR1 and the power supply wire PL. The capacitor CP stores charges, the amount of which corresponds to a difference between the data signal delivered from the first transistor TR1 and a first power signal applied to the power supply wire PL.

The second transistor TR2 is connected to the first transistor TR1, the capacitor CP, and the light emitting element OLED. The second transistor TR2 controls a driving current flowing through the light emitting element OLED in response to the amount of charge stored in the capacitor CP. A turn-on time of the second transistor TR2 may be determined depending on the amount of charges stored in the capacitor CP. The second transistor TR2 provides the light emitting element OLED with the first power signal delivered through the power supply wire PL during the turn-on time.

Depending on an electrical signal, the light emitting element OLED may generate a light and/or may control the amount of light. The light emitting element OLED may include an organic light emitting element or a quantum dot light emitting element.

The light emitting element OLED is connected to a power supply terminal VSS to receive a power signal (hereinafter referred to as a "second power signal") different from the first power signal provided through the power supply wire PL. A driving current corresponding to a difference between the electrical signal provided from the second transistor TR2 and the second power signal flows through the light emitting element OLED. Accordingly, the light emitting element OLED may generate light corresponding to the driving current. The pixel PX may include one or more other electronic elements and/or configurations and arrays.

The display pads PDD may include first pads D1 and a second pad D2. The first pads D1 may be connected to the data wires DL. The second pad D2 may be electrically connected to the power supply wire PL. The display panel DP may provide the pixels PX with electrical signals provided from the outside through the display pads PDD. The display pads PDD may further include pads for receiving other electrical signals in addition to the first pads D1 and the second pad D2.

Referring to FIG. 4B, the display area AA of the display panel DP may include a first area A1 and a second area A2. The display area AA may be surrounded by the non-display area NAA.

The second area A2 may be positioned closer to the non-display area NAA than the first area A1. The second area A2 may be positioned between the first area A1 and the non-display area NAA in a plan view. The second area A2 may surround the first area A1. The second area A2 may be positioned at one or more edges of the display area AA. A width of the second area A2 may be configured according to particular embodiments.

The first area A1 may correspond to a main display area. The second area A2 may correspond to a supplemental display area for the biometric information measurement mode. The first area A1 may display red light, green light, and blue light. The second area A2 may display only blue light. In the biometric information measurement mode, the second area A2 may emit light with high power.

Figure 5A:
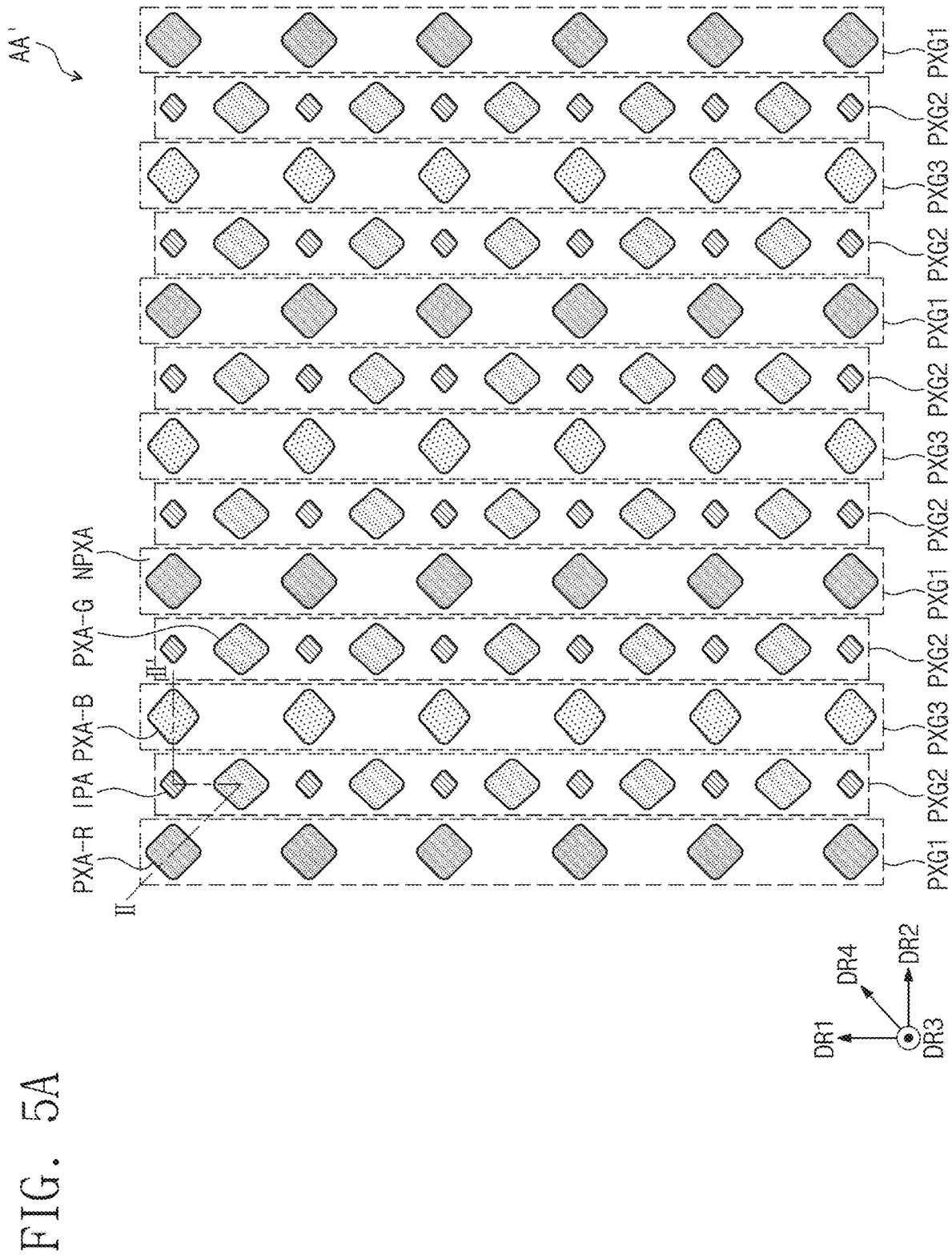
FIG. 5A is a plan view of an area AA' of FIG. 4B according to an embodiment.
Figure 5B:
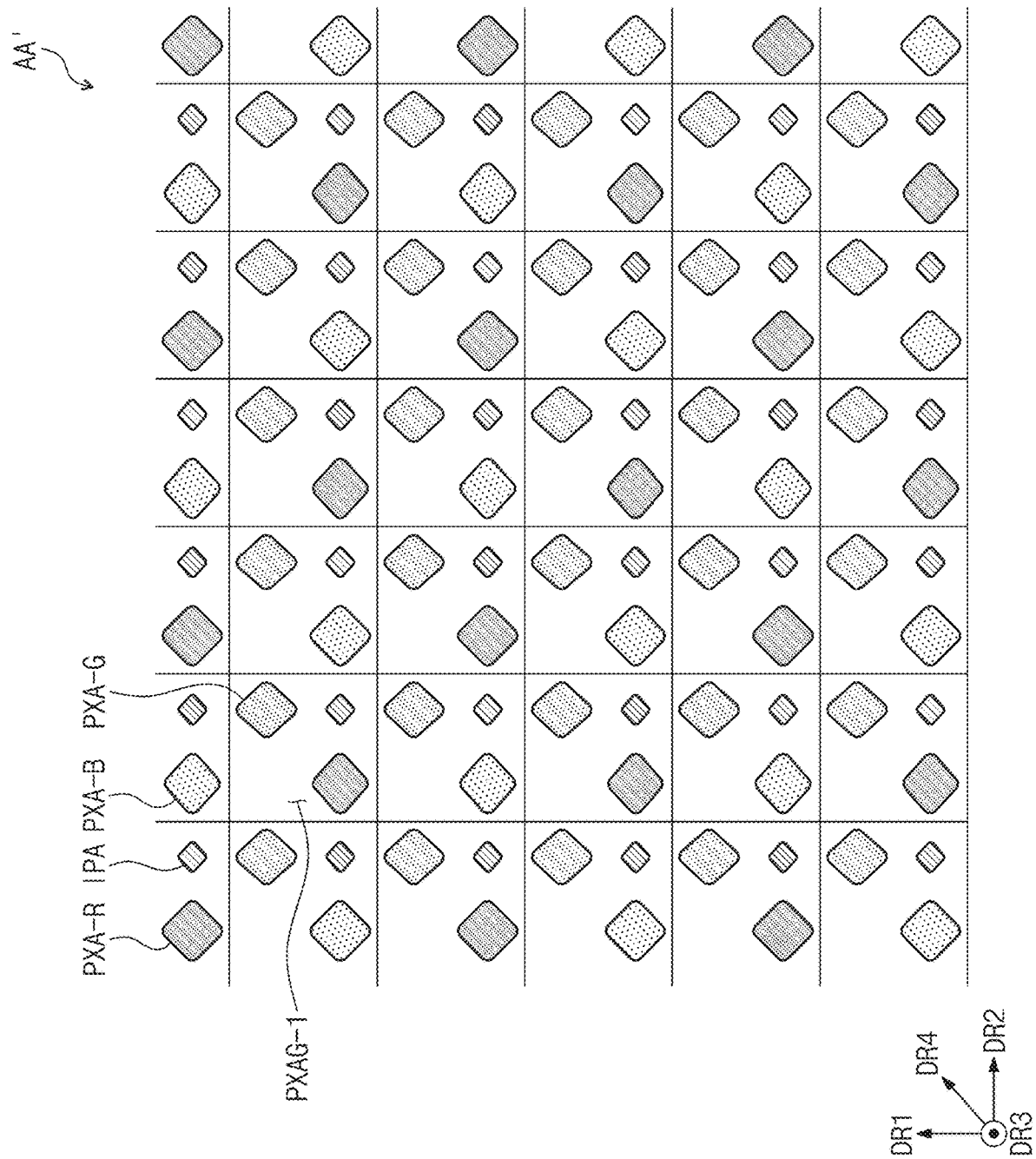
FIG. 5B is a plan view of the area AA' of FIG. 4B according to an embodiment.
Figure 5C:
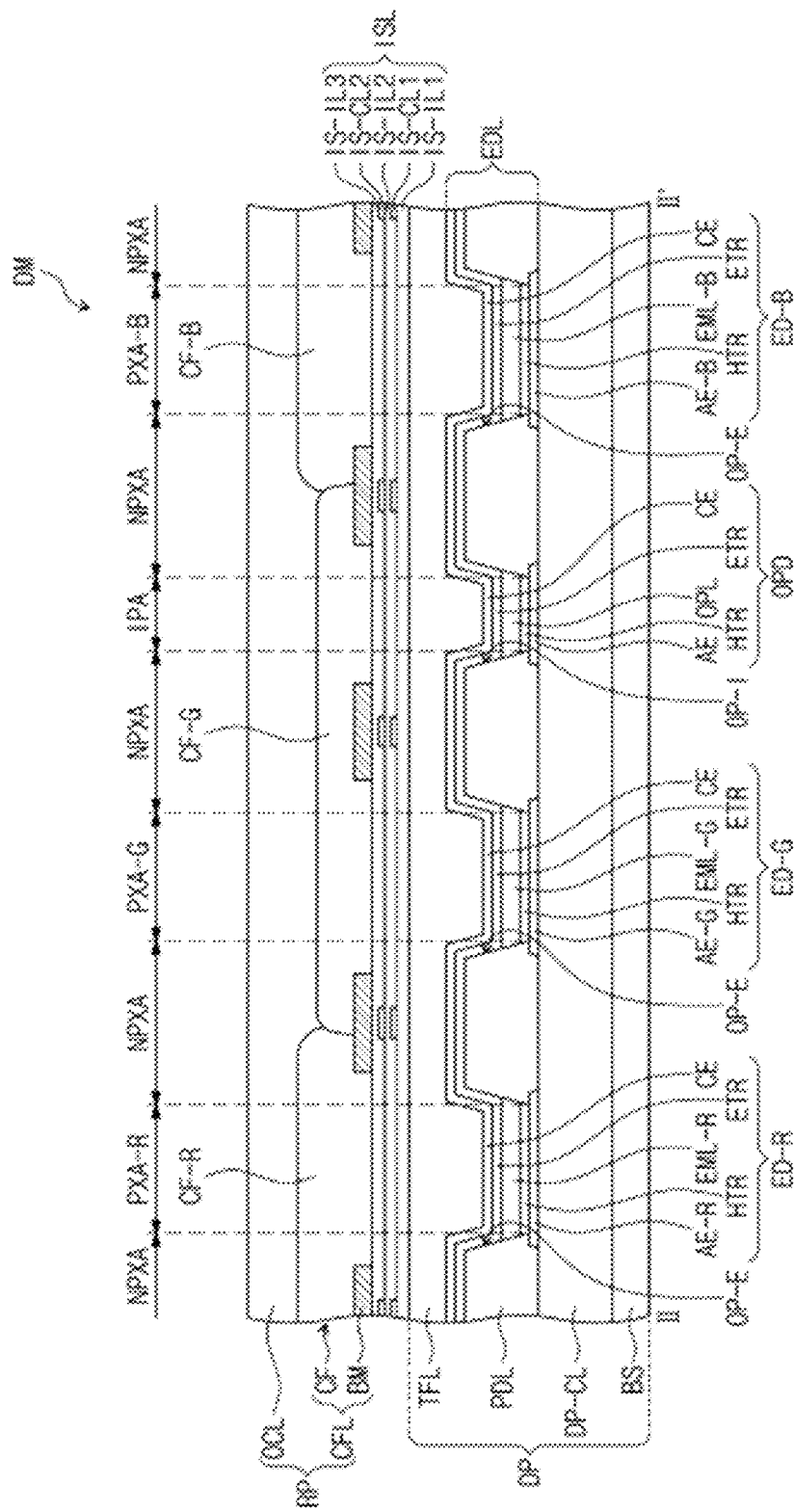
FIG. 5C is a cross-sectional view taken along a line II-II' of FIG. 5A according to an embodiment.

FIGS. 5A and 5B are plan views of an area AA' of FIG. 4B according to one or more embodiments. FIG. 5C is a cross-sectional view taken along a line II-II' of FIG. 5A according to an embodiment.

FIGS. 5A, 5B, and 5C illustrate light emitting areas PXA-R, PXA-G, and PXA-B and a light receiving area IPA, which are positioned in the first area A1 of the display area AA. In the first area A1, the display module DM may include the red light emitting area PXA-R for emitting red light, the green light emitting area PXA-G for emitting green light, and the blue light for emitting area PXA-B emitting blue light. The display module DM may include the light receiving area IPA for receiving and detecting reflected light that is reflected from an external object. The display panel DP (see FIG. 4A) may include a plurality of unit pixels. Each of the unit pixels may include a light receiving area IPA and may include a red light emitting area PXA-R, a green light emitting area PXA-G, and a blue light emitting area PXA-B, which may surround the light receiving area IPA. The one light receiving area IPA and the red light emitting area PXA-R, the green light emitting area PXA-G, and the blue light emitting area PXA-B may constitute one unit pixel. A unit pixel area including the unit pixel is illustrated in FIG. 5C.

A non-light emitting area NPXA (or non-emitting area NPXA) may be positioned between two of the areas PXA-R, PXA-G, PXA-B, and IPA. The areas IPA, PXA-R, PXA-G, and PXA-B may be separated from each other by a non-light emitting area NPXA. A non-light emitting area NPXA may surround each of the areas PXA-R, PXA-G, PXA-B, and IPA.

Sizes of light emitting areas that emit light of different wavelength ranges may be different in a plan view of the display panel DP. Sizes of light emitting areas PXA-R, PXA-G, and PXA-B may be different from each other in a plan view of the display panel DP.

The light emitting areas PXA-R, PXA-G, and PXA-B may have the same area size as one another. The light emitting areas PXA-R, PXA-G, and PXA-B may emit light of a color other than red light, green light, and blue light and/or may have a planar shape different from the illustrated shape(s).

An area size of a light receiving area IPA on a plane may be smaller than an area size of each of a red light emitting area PXA-R, a blue light emitting area PXA-B, and a green light emitting area PXA-G in a plan view of the display panel DP. An area size of a light receiving area IPA may be equal to or greater than that of one of a red light emitting area PXA-R, a blue light emitting area PXA-B, and a green light emitting area PXA-G in a plan view of the display panel DP.

Referring to FIG. 5A, red light emitting areas PXA-R may be spaced from one another in the first direction axis DR1 and may constitute a first group PXG1. Green light emitting areas PXA-G and the light receiving areas IPA may be alternately positioned in the first direction axis DR1 and may constitute a second group PXG2. Blue light emitting areas PXA-B may be spaced from one another in the first direction axis DR1 and may constitute a third group PXG3.

The first to third groups PXG1 to PXG3 may be arranged in the second direction axis DR2. A plurality of first groups PXG1 may be provided; a plurality of second groups PXG2 may be provided; a plurality of third groups PXG3 may be provided. Referring to FIG. 5A, sets including a first group PXG1, a second group PXG2, a third group PXG3, and a second group PXG2 may be arranged in the second direction axis DR2.

A green light emitting area PXA-G may be positioned spaced from a red light emitting area PXA-R and/or a blue light emitting area PXA-B in the fourth direction axis DR4. The fourth direction axis DR4 may be a direction between the first direction axis DR1 and the second direction axis DR2 and may be oblique relative to each of the direction axes DR1 and DR2.

A light receiving area IPA may be spaced from each of light emitting areas PXA-R, PXA-G, and PXA-B. Light receiving areas IPA may each be positioned between a red light emitting area PXA-R and a blue light emitting area PXA-B and may be spaced from each other in a second direction axis DR2. Light receiving areas IPA and green light emitting areas PXA-G may be alternately arranged in the first direction axis DR1.

The arrangement structure of the light emitting areas PXA-R, PXA-G, and PXA-B shown in FIG. 5A may be referred to as a "PENTILE structure".

Light emitting areas PXA-R, PXA-G, and PXA-B may be arranged in a stripe structure, in which the red light emitting area PXA-R, the green light emitting area PXA-G, and the blue light emitting area PXA-B are alternately arranged in the first direction axis DR1 or the second direction axis DR2. In the stripe arrangement structure, a light receiving area IPA may be positioned in the same row or the same column as a green light emitting area PXA-G.

Referring to FIG. 5B, a red light emitting area PXA-R or a blue light emitting area PXA-B, a green light emitting area PXA-G, and a light receiving area IPA may define/form a unit pixel group PXAG-1. In the unit pixel group PXAG-1, the light receiving area IPA may be adjacent to the light emitting areas. Unit pixel groups PXAG-1 may be arranged in the first direction DR1 and the second direction DR2.

Referring to FIG. 5B, a unit pixel group PXAG-1 may include a green light emitting area PXA-G and a light receiving area IPA adjacent to each other. Unit pixel groups PXAG-1 may alternately include a red light emitting area PXA-R and a blue light emitting area PXA-B. Red light emitting areas PXA-R and blue light emitting areas PXA-B may be alternately arranged in the first direction DR1 and the second direction DR2.

FIG. 5C illustrates a cross-sectional view of a unit pixel of FIG. 5A according to an embodiment. The cross-sectional view of FIG. 5C shows the light emitting areas PXA-R, PXA-G, and PXA-B and the light receiving area IPA included in a unit pixel in the first area A1 shown in FIG. 5A. FIG. 5C is a cross-sectional view illustrating a part of the electronic device ED shown in FIG. 1, FIG. 2A, FIG. 2B, and/or FIG. 3 according to one or more embodiments.

The electronic device ED includes the base layer BS in the display module DM. The base layer BS may support the display element layer EDL. The base layer BS may be/include a glass substrate, a metal substrate, a polymer substrate, or the like. The base layer BS may be/include an inorganic layer, an organic layer, or a composite material layer.

The base layer BS may have a multi-layer structure. The base layer BS may have a three-layer structure including a synthetic resin layer, an adhesive layer, and a synthetic resin layer. The synthetic resin layer may include polyimide-based resin. The synthetic resin layer may include at least one of acrylate-based resin, methacrylate-based resin, polyisoprene-based resin, vinyl-based resin, epoxy-based resin, urethane-based resin, cellulose-based resin, siloxane-based resin, polyamide-based resin, and perylene-based resin. A "~~-based resin" includes the functional group of "~~".

The circuit layer DP-CL is disposed on the base layer BS. The circuit layer DP-CL may include an insulating layer, a semiconductor pattern, a conductive pattern, a signal line, and the like. An insulating layer, a semiconductor layer, and a conductive layer may be formed on the base layer BS through a coating or deposition process. Afterward, the insulating layer, the semiconductor layer, and the conductive layer may be selectively patterned through a plurality of photolithography processes. Afterward, the semiconductor pattern, the conductive pattern, and the signal line included in the circuit layer DP-CL may be formed.

The display element layer EDL may be disposed on the circuit layer DP-CL. The display element layer EDL may include light emitting elements ED-R, ED-G, and ED-B and a light receiving element OPD. Each of the light emitting elements ED-R, ED-G, and ED-B may include an organic light emitting element, a quantum dot light emitting element, a micro LED light emitting element, or a nano LED light emitting element. Each of the light emitting elements ED-R, ED-G, and ED-B may emit light according to an electrical signal.

The light receiving element OPD may be a light sensor that receives and recognizes light reflected by an external object. The light receiving element OPD may be a light sensor that recognizes light in a visible light range. The light receiving element OPD may be a biometric sensor that recognizes light reflected from a user's body part, such as a fingerprint or vein, and converts a light signal into an electrical signal. The light receiving element OPD may recognize the light reflected from acne bacteria in the user's skin US; the user's skin US is indicated in FIG. 1.

The light receiving element OPD may recognize red light and/or green light reflected from acne bacteria in the user's skin. The light reflected from acne bacteria in the user's skin may appear as red light or green light depending on the degree of inflammation progression.

The display element layer EDL includes a pixel defining layer PDL that includes openings OP-E and OP-I. The light emitting elements ED-R, ED-G, and ED-B and the light receiving element OPD may be separated by portions of the pixel defining layer PDL. The first openings OP-E may accommodate the light emitting elements ED-R, ED-G, and ED-B. The second opening OP-I may accommodate the light receiving element OPD.

The pixel defining layer PDL may be disposed on the circuit layer DP-CL. The openings OP-E and OP-I may partially expose upper surfaces of first electrodes AE-R, AE-G, AE-B, and AE. The light emitting areas PXA-R, PXA-G, and PXA-B and the light receiving area IPA may correspond to the areas of the first electrodes AE-R, AE-G, AE-B, and AE exposed by the openings OP-E and OP-I.

The pixel defining layer PDL may be formed of a polymer resin. The pixel defining layer PDL may include a polyacrylate-based resin or a polyimide-based resin. The pixel defining layer PDL may include an inorganic material in addition to the polymer resin. The pixel defining layer PDL may include a light absorbing material and/or may include a black pigment or a black dye. The pixel defining layer PDL may be a black pixel defining layer. Carbon black or the like may be used as the black pigment or the black dye.

The pixel defining layer PDL may be formed of an inorganic material. The pixel defining layer PDL may include silicon nitride (SiNx), silicon oxide (SiOx), silicon oxynitride (SiOxNy), and/or the like.

The red light emitting element ED-R includes the first electrode AE-R, (a portion of) a second electrode CE, and a light emitting layer EML-R; the green light emitting element ED-G includes the first electrode AE-G, (a portion of) the second electrode CE, and a light emitting layer EML-G; the blue light emitting element ED-B includes the first electrode AE-B, (a portion of) the second electrode CE, and a light emitting layer EML-B. The first electrodes AE-R, AE-G, and AE-B may be referred to as "light emitting element electrodes." The display element layer EDL may include the red light emitting element ED-R corresponding to the red light emitting area PXA-R and for emitting red light, the green light emitting element ED-G corresponding to the green light emitting area PXA-G and for emitting green light, and the blue light emitting element ED-B corresponding to the blue light emitting area PXA-B and for emitting blue light.

The first electrode AE-R and the second electrode CE overlap each other. The red light emitting layer EML-R is interposed between the first electrode AE-R and the second electrode CE. The first electrode AE-G and the second electrode CE overlap each other. The green light emitting layer EML-G is interposed between the first electrode AE-G and the second electrode CE. The first electrode AE-B and the second electrode CE overlap each other. The blue light emitting layer EML-B is interposed between the first electrode AE-B and the second electrode CE.

The light receiving element OPD may include the first electrode AE, (a portion of) the second electrode CE, and a light receiving layer OPL. The first electrode AE may be referred to as a "light receiving element electrode".

In the display element layer EDL, the first electrodes (AE-R, AE-G, AE-B, and AE) may be formed of a metal material, a metal alloy, or a conductive compound. Each of the first electrodes (AE-R, AE-G, AE-B, and AE) may be an anode or a cathode. Each of the first electrodes (AE-R, AE-G, AE-B, and AE) may be a pixel electrode or a sensing electrode. Each of the first electrodes (AE-R, AE-G, AE-B, and AE) may be a transmissive electrode, a transflective electrode, or a reflective electrode. When a first electrode (AE-R, AE-G, AE-B, or AE) is a transmissive electrode, the first electrode (AE-R, AE-G, AE-B, or AE) may include a transparent metal oxide, for example, indium tin oxide (ITO), indium zinc oxide (IZO), zinc oxide (ZnO), indium tin zinc oxide (ITZO), or the like. When the first electrode (AE-R, AE-G, AE-B, or AE) is a transflective electrode or a reflective electrode, the first electrode (AE-R, AE-G, AE-B, or AE) may include Ag, Mg, Cu, Al, Pt, Pd, Au, Ni, Nd, Ir, Cr, Li, Ca, LiF—Ca, LiF—Al, Mo, Ti, W or an alloy (e.g., an alloy of Ag and Mg).

The second electrode CE may be a common electrode. The second electrode CE may be a cathode or an anode. When the first electrode (AE-R, AE-G, AE-B, or AE) is an anode, the second electrode CE may be a cathode. When the first electrode (AE-R, AE-G, AE-B, or AE) is the cathode, the second electrode CE may be the anode.

The second electrode CE may be a transmissive electrode, a transflective electrode, or a reflective electrode. When the second electrode CE is a transmissive electrode, the second electrode CE may be formed of a transparent metal oxide, for example, indium tin oxide (ITO), indium zinc oxide (IZO), zinc oxide (ZnO), indium tin zinc oxide (ITZO), or the like. When the second electrode CE is a transflective electrode or a reflective electrode, the second electrode CE may include Ag, Mg, Cu, Al, Pt, Pd, Au, Ni, Nd, Ir, Cr, Li, Ca, LiF—Ca, LiF—Al, Mo, Ti, Yb, W, or an alloy (e.g., AgMg, AgYb, or MgAg).

The first electrode (AE-R, AE-G, AE-B, or AE) may be a transflective electrode or a reflective electrode. The second electrode CE may be a transmissive electrode or a transflective electrode. Light reflected from an external object may be easily transmitted to the light receiving element OPD.

The light emitting layers (EML-R, EML-G, and EML-B) of the light emitting elements (ED-R, ED-G, and ED-B) may be disposed in the first openings OP-E. The light emitting layers EML-R, EML-G, and EML-B may be separately formed in the first openings OP-E. Each of the light emitting layers EML-R, EML-G, and EML-B may include an organic light emitting material or a quantum dot material.

Each of the light emitting elements ED-R, ED-G, and ED-B may include a hole transport area HTR and an electron transport area ETR. The hole transport area HTR may be interposed between the first electrode (AE-R, AE-G, or AE-B) and the light emitting layer (EML-R, EML-G, or EML-B). The electron transport area ETR may be interposed between the light emitting layer (EML-R, EML-G, or EML-B) and the second electrode CE.

The light receiving layer OPL may be interposed between the first electrode AE and the second electrode CE and may be disposed in the second opening OP-I. The light receiving layer OPL may include a light receiving material that receives light and converts the light into an electrical signal. The light receiving layer OPL may include an organic light receiving material. The light receiving layer OPL may include an organic polymer material as a light receiving material. The light receiving layer OPL may include a conjugated polymer. The light receiving layer OPL may include thiophene-based conjugated polymer, benzodithiophene-based conjugated polymer, thieno[3,4-c] pyrrole-4,6-dione (TPD)-based conjugated polymer, diketo-pyrrolepyrrole (DPP)-based conjugated polymer, benzothiadiazole (BT)-based conjugated polymer, or the like.

The light receiving element OPD may include the hole transport area HTR and the electron transport area ETR. The hole transport area HTR may be interposed between the first electrode AE and the light receiving layer OPL. The electron transport area ETR may be interposed between the light receiving layer OPL and the second electrode CE.

A hole transport area HTR may have a single layer made of a single material, a single layer made of different materials, or a multi-layer structure including layers made of different materials. The hole transport area HTR may have a single-layer structure of a hole injection layer or a hole transport layer and may have a single-layer structure composed of a hole injection material and a hole transport material. The hole transport area HTR may include a hole transport layer and a hole injection layer.

An electron transport area ETR may have a single layer made of a single material, a single layer made of different materials, or a multi-layer structure including layers made of different materials.

The electron transport area ETR may have a single-layer structure of an electron injection layer or an electron transport layer and may have a single-layer structure composed of an electron injection material and an electron transport material. The electron transport area ETR may include a plurality of layers that are sequentially stacked on the light emitting layer (EML-R, EML-G, or EML-B). The electron transport area ETR may include an electron transport layer and an electron injection layer.

Referring to FIG. 5C, a hole transport area HTR may be disposed on/under the light emitting layer (EML-R, EML-G, or EML-B) of each of the light emitting elements (ED-R, ED-G, and ED-B) or the light receiving layer OPL of the light receiving element OPD. The hole transport areas HTR may be separated by the pixel defining layer PDL. The electron transport area ETR may be a common layer for the light emitting elements (ED-R, ED-G, and ED-B) and the light receiving element OPD. The electron transport area ETR may overlap the pixel defining layer PDL, the light emitting layers (EML-R, EML-G, and EML-B), and the light receiving layer OPL.

The encapsulation layer TFL may be disposed on the display element layer EDL. The encapsulation layer TFL may include at least one inorganic layer and at least one organic layer. The encapsulation layer TFL may include a first inorganic layer, an organic layer, and a second inorganic layer sequentially stacked.

The input sensing layer ISL may be disposed on the display element layer EDL. The input sensing layer ISL may detect an external input applied from the outside. The external input may be a user input. The user input may be related to a part of a user body, light, heat, a pen, or pressure.

The input sensing layer ISL may be formed on the display panel DP through sequential processes. The input sensing layer ISL may be directly disposed on the display panel DP. No adhesive member may be interposed between the input sensing layer ISL and the display panel DP. The input sensing layer ISL may be disposed directly on the encapsulation layer TFL.

An adhesive member (not shown) may be interposed between the input sensing layer ISL and the display panel DP.

The input sensing layer ISL may include a lower insulating layer IS-IL1, a first conductive layer IS-CL1, an interlayer insulating layer IS-IL2, a second conductive layer IS-CL2, and an upper insulating layer IS-IL3. At least one of the lower insulating layer IS-IL1 and the upper insulating layer IS-IL3 may be optional.

Each of the first conductive layer IS-CL1 and the second conductive layer IS-CL2 may have a single-layer structure or may have a structure in which multiple layers are stacked along the third direction DR3. A conductive layer having a multi-layer structure may include at least two transparent conductive layers and/or metal layers. The conductive layer may include metal layers including different metals. A transparent conductive layer may include indium tin oxide (ITO), indium zinc oxide (IZO), zinc oxide (ZnO), indium tin zinc oxide (ITZO), PEDOT, metal nanowires, or graphene. A metal layer may include molybdenum, silver, titanium, copper, aluminum, or an alloy of some of the above metals. For example, each of the first conductive layer IS-CL1 and the second conductive layer IS-CL2 may have a three-layer structure, for example, a three-layer structure of titanium-aluminum-titanium. A metal having relatively high durability and low reflectance may be used for an upper/lower layer. A metal having high electrical conductivity may be used for an inner layer.

Each of the first conductive layer IS-CL1 and the second conductive layer IS-CL2 includes a plurality of conductive members. The first conductive layer IS-CL1 includes first conductive members, and the second conductive layer IS-CL2 includes second conductive members. The first conductive members may include sensing electrodes and signal lines connected to the sensing electrodes. The second conductive members may include sensing electrodes and signal lines connected to the sensing electrodes. The first conductive members and the second conductive members may be covered by a light blocking part BM. The light blocking part BM may prevent external light from being reflected by the first conductive layer IS-CL1 and the second conductive layer IS-CL2.

Each of the lower insulating layer IS-IL1, the interlayer insulating layer IS-IL2, and the upper insulating layer IS-IL3 may include an inorganic film or an organic film. The lower insulating layer IS-IL1 and the interlayer insulating layer IS-IL2 may be inorganic films. The upper insulating layer IS-IL3 may include an organic film.

The anti-reflection member RP is disposed on the display panel DP. The anti-reflection member RP may be directly disposed on the input sensing layer ISL. The anti-reflection member RP may include the color filter layer CFL and the organic planarization layer OCL.

The color filter layer CFL may include filter parts CF and the light blocking part BM. The filter parts CF may include a red filter part CF-R, a green filter part CF-G, and a blue filter part CF-B. The red filter part CF-R, the green filter part CF-G, and the blue filter part CF-B may correspond to the red light emitting area PXA-R, the green light emitting area PXA-G, and the blue light emitting area PXA-B, respectively. The green filter part CF-G may overlap the light receiving area IPA. The green filter part CF-G may overlap both the green light emitting element ED-G and the light receiving element OPD.

The red filter part CF-R may transmit red light; the green filter part CF-G may transmit green light; the blue filter part CF-B may transmit blue light. Each of the red filter part CF-R, the green filter part CF-G, and the blue filter part CF-B may include a polymer photosensitive resin and a pigment or dye. The red filter part CF-R may include a red pigment or dye; the green filter part CF-G may include a green pigment or dye; the blue filter part CF-B may include a blue pigment or dye.

The blue filter part CF-B may not include a pigment or dye. The blue filter part CF-B may include a polymer photosensitive resin and may not include a pigment or dye. The blue filter part CF-B may be transparent. The blue filter part CF-B may be formed of a transparent photosensitive resin.

The light blocking part BM may be disposed on the input sensing layer ISL and may overlap the boundaries of neighboring filter parts CF. Edges of neighboring filter parts CF may overlap each other. Portions of the green filter part CF-G and the red filter part CF-R may be disposed on the light blocking part BM and may overlap each other. Portions of the green filter part CF-G and the blue filter part CF-B may be disposed on the light blocking part BM and may overlap each other. The light blocking part BM may prevent light leakage and may identify the boundaries between adjacent color filter parts (CF-R, CF-G, and CF-B).

The light blocking part BM may be a black matrix. The light blocking part BM may include an organic pigment or dye. The light blocking part BM may include an organic light blocking material or an inorganic light blocking material that includes a black pigment or a black dye. The light blocking part BM may include a light blocking composition including propylene glycol monomethyl ether acetate, 3-methoxybutyl acetate, and an organic black pigment.

The light blocking part BM may overlap portions of the pixel defining layer PDL that are positioned between the light emitting areas PXA-R, PXA-G, and PXA-B and the light receiving area IPA.

The organic planarization layer OCL may be disposed on the color filter layer CFL, may protect the color filter parts (CF-R, CF-G, and CF-B), and may planarize an upper surface of the color filter layer CFL. The organic planarization layer OCL may include an organic material such as an acrylic resin or an epoxy resin. The organic planarization layer OCL may be formed by photocuring or thermosetting the organic material. The organic planarization layer OCL may be/include a single layer or a plurality of layers.

Figure 6A:
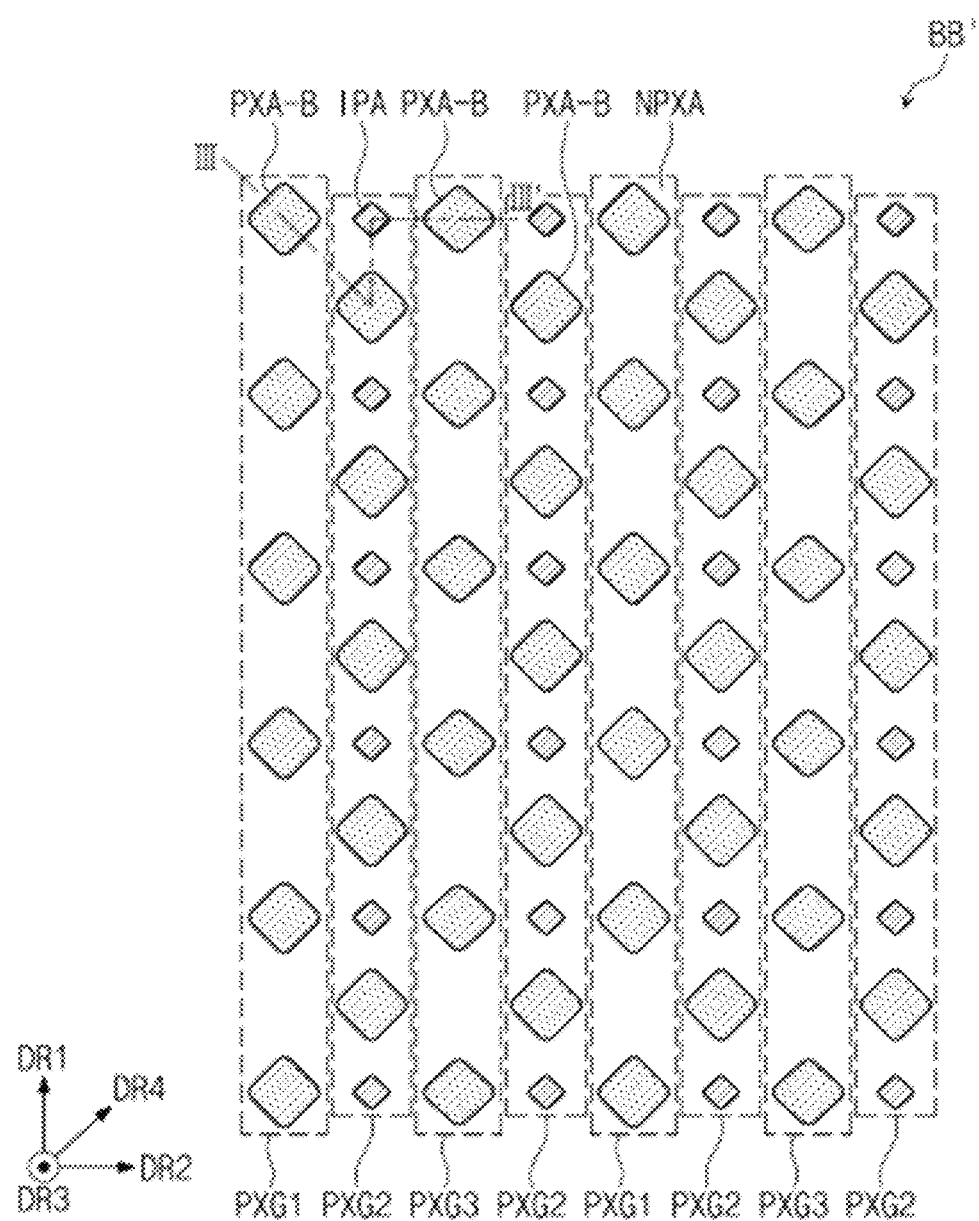
FIG. 6A is a plan view of an area BB' of FIG. 4B according to an embodiment.
Figure 6B:
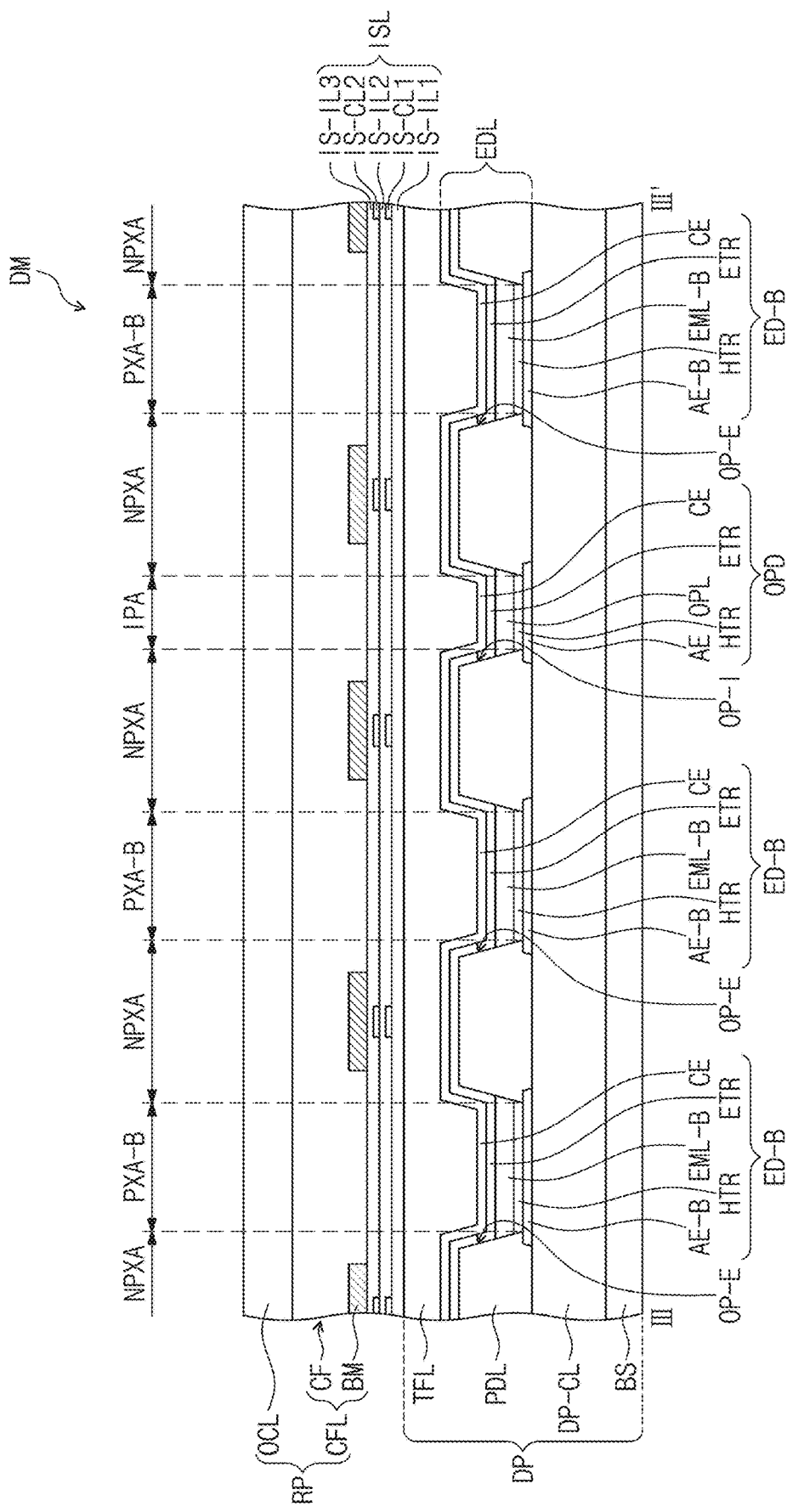
FIG. 6B is a cross-sectional view taken along a line III-III' of FIG. 6A according to an embodiment.

FIG. 6A is a plan view of an area BB' of FIG. 4B according to an embodiment. FIG. 6B is a cross-sectional view taken along a line III-III' of FIG. 6A according to an embodiment and illustrates a unit pixel area including a unit pixel. Some features illustrated in FIGS. 6A and 6B may be identical to or analogous to some features described with reference to FIGS. 5A and 5C.

FIGS. 6A and 6B illustrate light emitting areas PXA-B and light receiving areas IPA positioned in the second area A2 of the display area AA. In the second area A2, the display module DM may include blue light emitting areas PXA-B for emitting blue light without including red light emitting areas or green light emitting areas. The second area A2 of the display module DM may include a light receiving area IPA for receiving and detecting light reflected from an external object. The light receiving area IPA may be surrounded by blue light emitting areas PXA-B. A unit pixel in the second area A2 may include the light receiving area IPA and blue light emitting areas PXA-B surrounding the light receiving area IPA.

Referring to FIG. 4B and FIG. 6A, blue light emitting areas PXA-B, but no red light emitting areas or green light emitting areas, may be included in a unit pixel area (indicated by a line III-III') in the second area A2. The number of the blue light emitting areas PXA-B included in a unit pixel area in the second area A2 is greater than the number of the blue light emitting areas PXA-B included in a unit pixel area (indicated by a line II-II') in the first area A1 (shown in FIG. 4B and FIG. 5A). One blue light emitting area PXA-B may be included in a unit pixel area (indicated by the line II-II') in the first area A1. Three blue light emitting areas PXA-B may be included in a unit pixel area (indicated by a line III-III') in the second area A2. Blue light emission areas per unit pixel area or per unit area (e.g., 1 cm^2) of the second area A2 may be greater than blue light emission areas per unit pixel area or per unit area (e.g., 1 cm^2) of the first area A1. The density of blue light emission areas in the second area A2 may be greater than the density of blue light emission areas in the first area A1. In the second area A2, a light receiving area IPA immediately neighbors at least two blue light emitting areas PXA-B without any red or green light emitting area being positioned between the light receiving area IPA and the two blue light emitting areas PXA-B.

Referring to FIG. 6B, the display element layer EDL within the unit pixel area in the second area A2 may include blue light emitting elements ED-B in the blue light emitting areas PXA-B for emitting blue light.

The display element layer EDL may include a light receiving element OPD. The light receiving element OPD may selectively recognize red light and green light reflected from acne bacteria in the user's skin US; the user's skin US is indicated in FIG. 1. The light reflected from acne bacteria in the user's skin may appear as red light or green light depending on the degree of inflammation progression.

Figure 7:
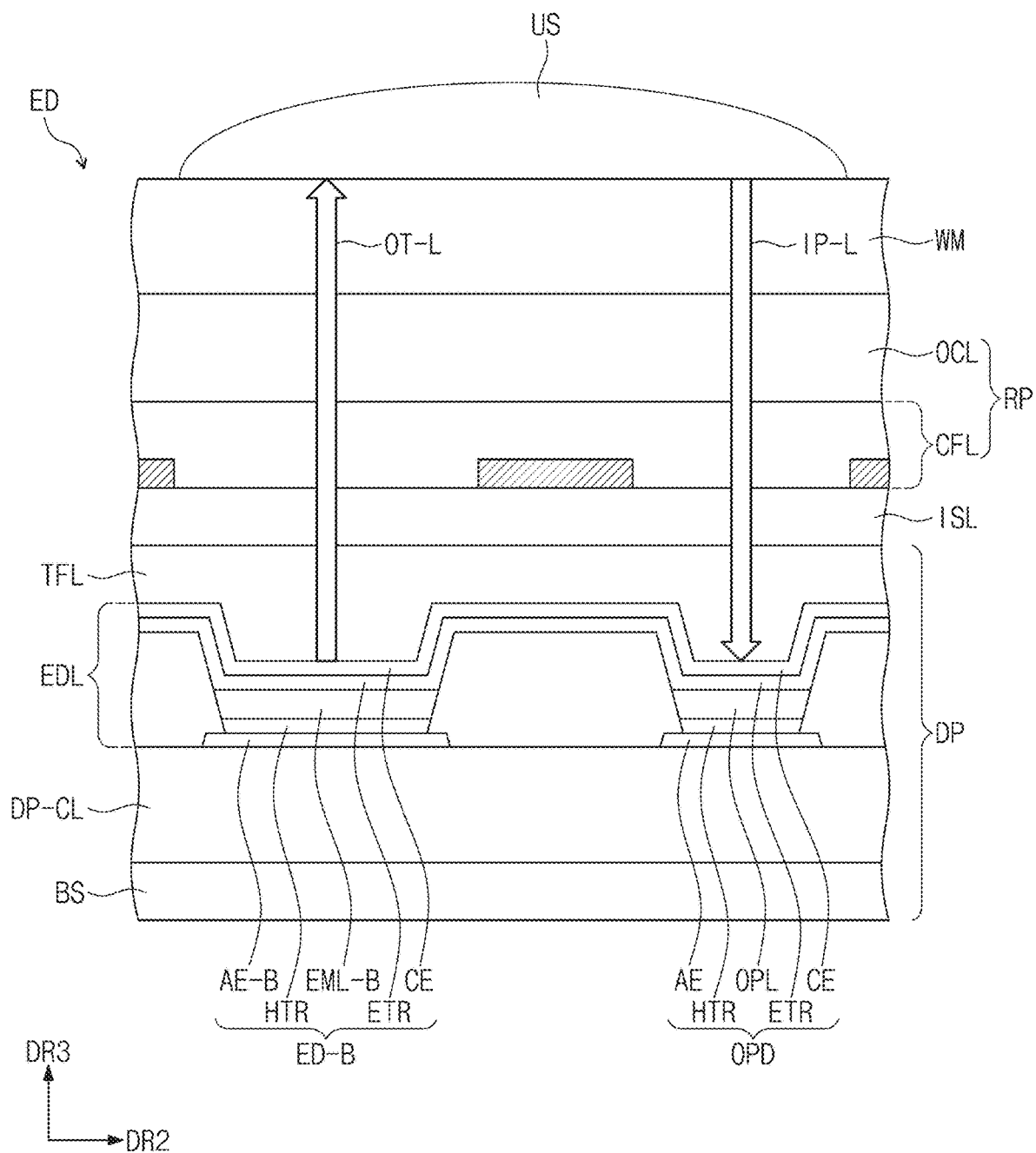
FIG. 7 is a cross-sectional view of an electronic device according to an embodiment.

FIG. 7 is a cross-sectional view of an electronic device according to an embodiment. FIG. 7 illustrates that a light receiving element OPD receives red light or green light reflected from acne bacteria in the skin US of a user.

Referring to FIG. 7, in the electronic device ED according to an embodiment, emitted light OT-L emitted from the blue light emitting element ED-B included in the display element layer EDL is at least partially reflected by an external object (e.g., the user's skin US) to produce reflected light IP-L. The reflected light IP-L is incident on the light receiving element OPD included in the display element layer EDL. The reflected light IP-L may be in a visible light range. The reflected light IP-L may be a red light or a green light. In response to the reflected light IP-L, the light receiving element OPD may generate and/or provide an electrical signal. Accordingly, the driving state of the electronic device ED may be changed.

Electrical signals generated and/or provided by light receiving elements OPD may be converted into an image by the biometric information measurement module BIM (shown in FIG. 3). The image may provide information about the location and/or inflammation type of acne bacteria in the skin US of the user.

When the light receiving element OPD receives green reflected light IP-L, the biometric information measurement module BIM may determine that the acne bacteria in the user's skin US is in a first inflammation state. When the light receiving element OPD receives red reflected light IP-L, the module BIM may determine that the acne bacteria in the user's skin US is in a second inflammation state. When green light of wavelength in a range of 570 nm to 630 nm is incident on the light receiving element OPD, acne bacteria may correspond to the first inflammation type in an initial stage indicated by coproporphyrin III. When red light of a wavelength of 630 nm or more is incident on the light receiving element OPD, acne bacteria may correspond to the second inflammation type in a progressed stage indicated by protoporphyrin. The coproporphyrin III in acne bacteria in the skin US of the user may absorb blue light and may emit green light as the reflected light IP-L. The protoporphyrin in acne bacteria in the skin US of the user may absorb blue light and may emit red light as the reflected light IP-L.

The biometric information measurement module BIM may determine status information of acne bacteria on the user's skin based on the received amount of the incident red light or the incident green light.

Figure 8:
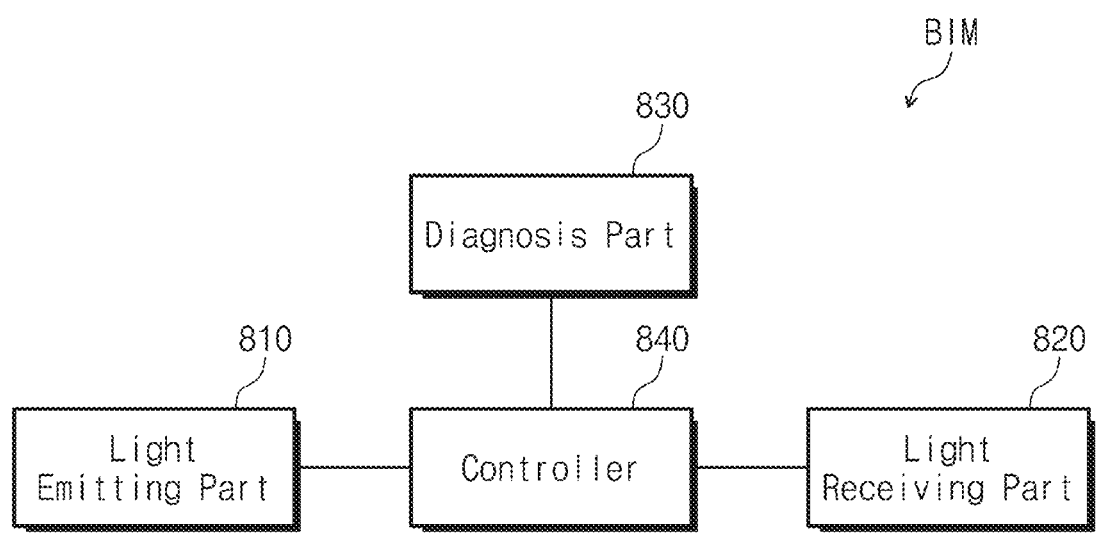
FIG. 8 is a block diagram of a biometric information measurement module according to an embodiment.

FIG. 8 is a block diagram of a biometric information measurement module BIM according to an embodiment.

Referring to FIG. 8, the biometric information measurement module BIM may include a light emitting part 810, a light receiving part 820, a diagnosis part 830, and a controller 840.

The light emitting part 810 may control blue light emitting elements ED-B to emit blue light and/or may emit blue light through blue light emitting elements ED-B (shown in FIG. 6B and FIG. 7). The light emitting part 810 and the light emitting module LM are electrically connected through a control module CM, and when the light emitting module LM emits light, the light emitting part 810 may receive a light emitting signal. In a biometric information measurement mode, the light emitting part 810 may control the blue light emitting elements ED-B (shown in FIG. 6B) to emit light in a high power mode.

The light receiving part 820 may control light receiving elements OPD to receive reflected light and/or may receive reflected light reflected from the user's skin US (see FIG. 7) through light receiving elements OPD (shown in FIG. 7). The light receiving part 820 may receive (signals related to) red reflected light or green reflected light through the light receiving element OPD. The light receiving part 820 and the light receiving module LRM are electrically connected through a control module CM, and when the light receiving module LRM receives light, the light receiving part 820 may receive a light receiving signal.

The diagnosis part 830 may determine biometric information including inflammation information of acne bacteria of the skin US of the user based on the reflection location, the color, and the amount of the received reflected light. The diagnosis part 830 may generate the user's skin condition image using the electrical signals associated with the reflected light reflected from the user's skin. The skin condition image may show a plurality of inflammations, of which the brightness depends on the light receiving amount of red light or green light. The skin condition image may show a plurality of first inflammations determined according to the reception of green light and a plurality of second inflammations determined according to the reception of red light.

The diagnosis part 830 may generate the user's skin condition information based on a skin condition image. The diagnosis part 830 may provide the user with the user's skin condition information by extracting information about the number and locations of the first inflammations and the number and locations of the second inflammation from the user's skin condition image. The diagnosis part 830 may diagnose the user's skin condition based on the extracted skin condition information of the user. Depending on the degree of inflammation of the user's acne bacteria, the diagnosis part 830 may make a customized prescription for the user's skin condition.

The controller 840 may control the overall process, including the transmission of signals or information between the light emitting part 810, the light receiving part 820, and the diagnosis part 830.

Figure 9:
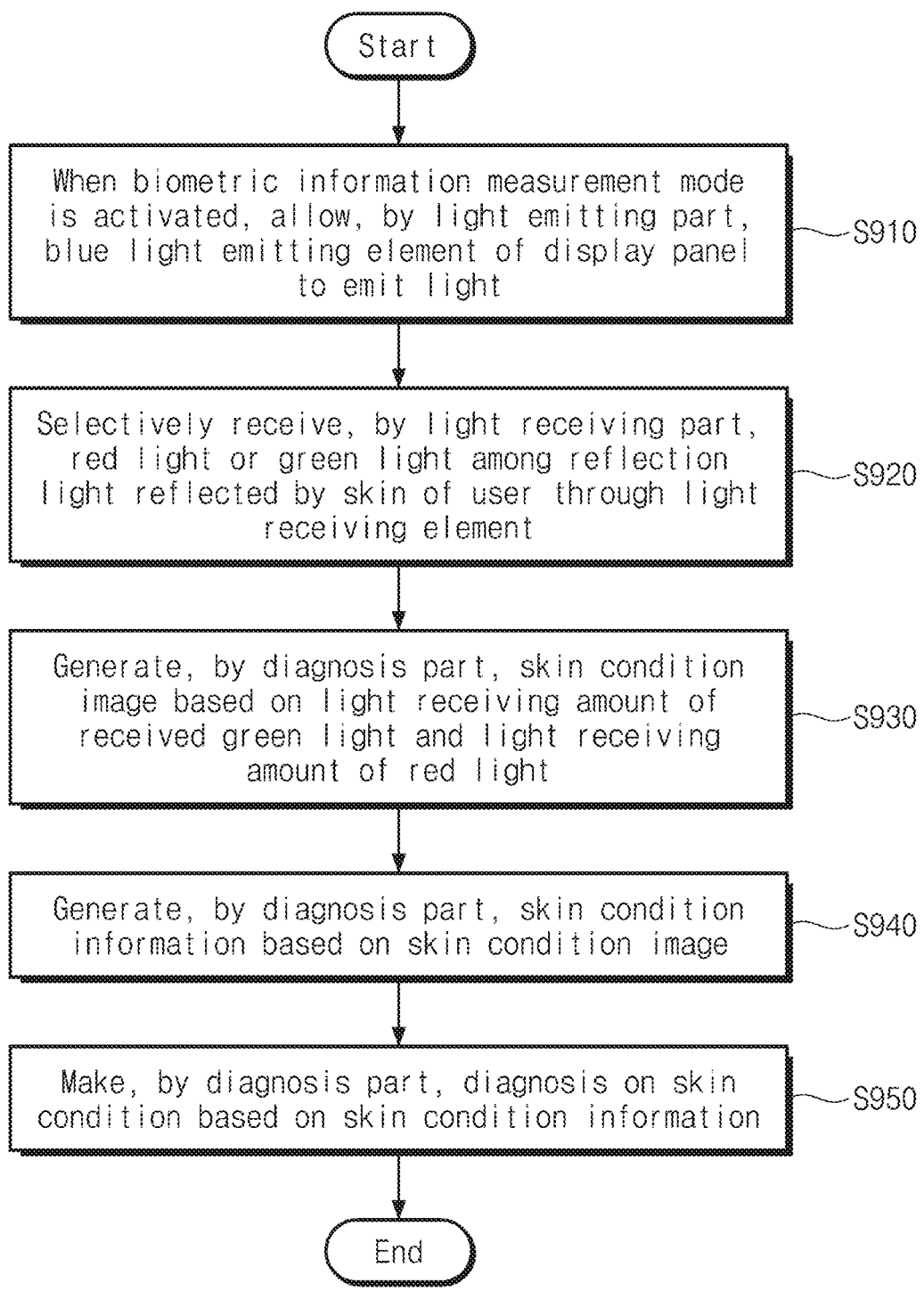
FIG. 9 is a flowchart illustrating a method for determining and/or generating biometric information according to an embodiment.
Figure 10:
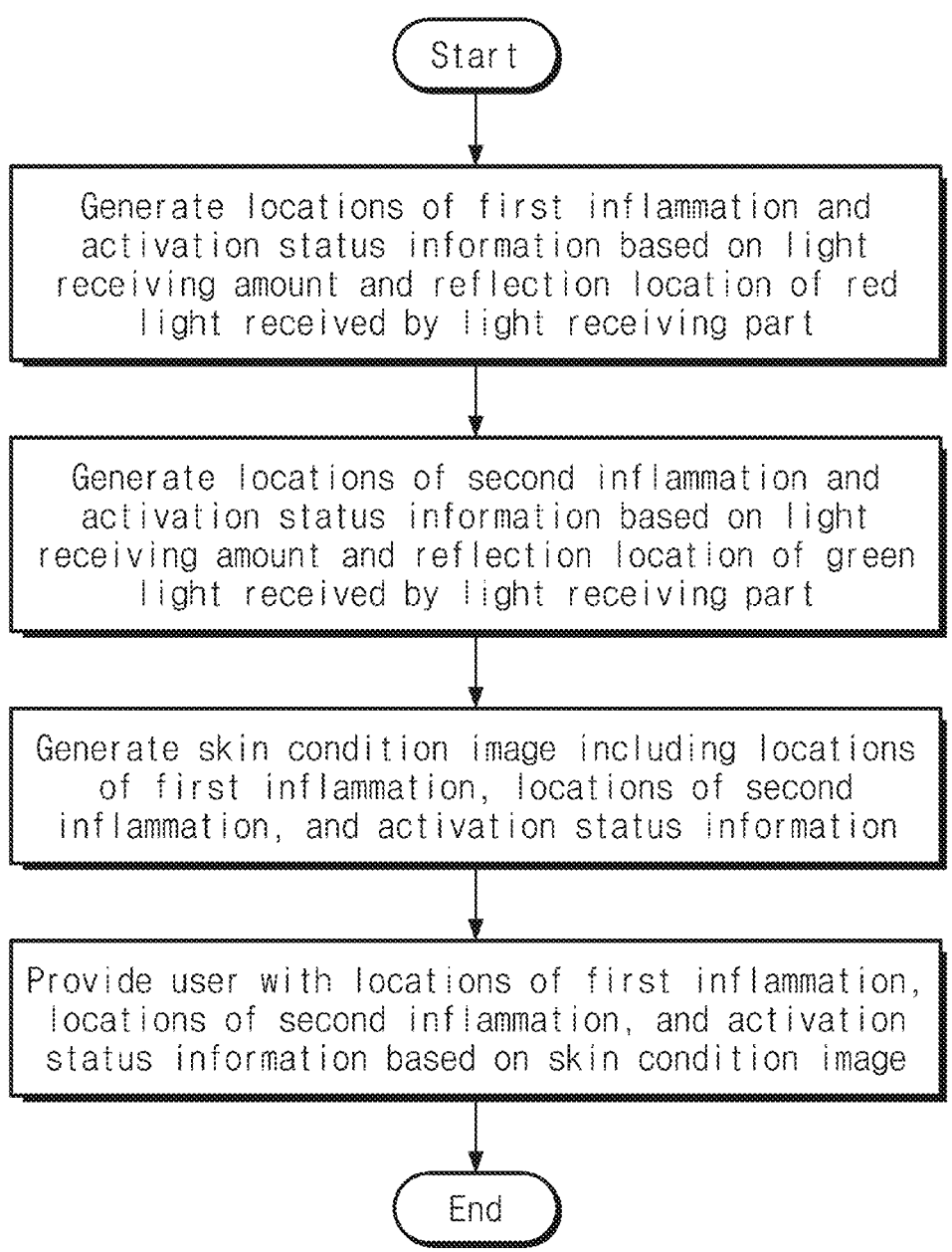
FIG. 10 is a flowchart illustrating a method for determining and/or generating biometric information according to an embodiment.

FIGS. 9 and 10 are flowcharts illustrating one or more methods for determining and/or generating biometric information according to one or more embodiments.

Referring to FIG. 9, when the biometric information measurement mode is activated depending on the control of a user, the light emitting part 810 may emit blue light through the blue light emitting elements ED-B in areas A1 and A2 of the display panel DP (operation/step S910). The light emitting part 810 may activate a high power mode and may allow the blue light emitting elements ED-B disposed in the second area A2 to emit blue light in a high power mode.

The light receiving part 820 may receive the reflected light reflected from acne bacteria in the skin US of the user through light receiving elements OPD (operation/step S920). The light receiving part 820 and/or the light receiving elements OPD may receive green light reflected from first inflammations or red light reflected from second inflammations according to acne bacteria in the skin US of the user.

Referring to FIG. 9 and FIG. 10, the diagnosis part 830 may generate a skin condition image indicating the locations and degree of the first inflammations and the locations and degree of the second inflammations based on the received green light and red light (operation/step S930). The diagnosis part 830 may generate the user's skin condition image based on the light receiving amount of reflected green light and the light receiving amount of reflected red light.

Referring to FIG. 9 and FIG. 10, the diagnosis part 830 may generate skin condition information of the user based on the generated skin condition image (operation/step S940). The user's skin condition information may include information about the locations and number of first inflammations and the locations and number of second inflammations identified in the skin condition image.

Referring to FIG. 9 and FIG. 10, the diagnosis part 830 may make a diagnosis on the status of the user's skin based on the skin condition information (operation/step S950). The diagnosis part 830 may determine a customized prescription based on biometric information including inflammation information about the user's acne bacteria. The diagnosis part 830 may diagnose the status of the user's skin depending on a predetermined algorithm, and may provide the user with customized prescription information according to the user's skin condition.

Figures 11A, 11B, 11C:
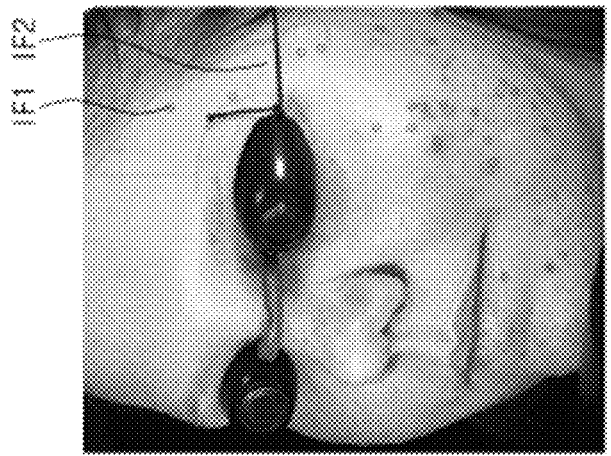
FIG. 11 shows photos illustrating skin conditions of a user according to one or more embodiments.

FIG. 11A, FIG. 11B, and FIG. 11C can show photos illustrating skin condition images according to one or more embodiments. Photos of FIG. 11A, FIG. 11B, and FIG. 11C are excerpts from "Measuring acne using Coproporphyrin III, Protoporphyrin IX, and lesion-specific inflammation: an exploratory study, Arch Dermatol Res (2017) 309:159-167".

FIG. 11A, shows a first inflammation IF1 and a second inflammation IF2 in a photo of a user. For FIG. 11B and FIG. 11C, to clearly show the locations of the first inflammation IF1 and the second inflammation IF2, the user's photo was processed in black and white. The first inflammation IF1 may correspond to coproporphyrin III, which indicates an initial stage, associated with acne bacteria in the user's skin. The second inflammation IF2 may correspond to protoporphyrin, which indicates a progressed state, associated with acne bacteria in the user's skin. Referring to FIG. 1 to FIG. 11C, an electronic device ED and a biometric information generation method according to one or more embodiments may provide the user with information related to the degree of inflammation of acne bacteria and inflammation locations of acne bacteria in the user's skin. The electronic device ED may effectively determine biometric information on acne bacteria in a user's skin using light emitting elements, light receiving elements, and a biometric information measurement module positioned inside the display panel DP.

Examples of embodiments have been described. Various changes and modifications may be made to the described embodiments without departing from the scope of the following claims.

What is claimed is:

1. An electronic device comprising:
   a display panel including red-light emitting elements, green-light emitting elements, blue-light emitting elements, and light receiving elements that are spaced from each other, wherein the blue-light emitting elements emit blue light in a biometric information measurement mode of the electronic device, wherein the light receiving elements receive at least one of red light and green light in the biometric information measurement mode of the electronic device after the blue-light emitting elements have emitted the blue light, and wherein the light receiving elements generate electrical signals in response to the at least one of the red light and the green light; and
   a biometric information measurement module electrically connected to the display panel and configured to generate biometric information about a skin of a user based on the electrical signals,
   wherein the display panel comprises a display area including a first area and a second area, a non-display area surrounding the display area,
   wherein the first area includes first red-light emitting elements, first green-light emitting elements, first blue-light emitting elements and a first light receiving element, and the second area includes a plurality of second blue-light emitting elements and a second light receiving element,
   wherein the plurality of the second blue-light emitting elements includes a first-second blue-light emitting element, a second-second blue-light emitting element, a third-second blue-light emitting element and a fourth-second blue-light emitting element,
   wherein the second light receiving element is interposed between the first-second blue-light emitting element and the second-second blue-light emitting element along a first direction, and is interposed between the third-second blue-light emitting element and the fourth-second blue-light emitting element along a second direction perpendicular to the first direction, and
   wherein the second area does not include red-light emitting elements and green-light emitting elements.

2. The electronic device of claim 1, wherein the biometric information measurement module determines an inflammation state of a location of the skin of the user based on whether light reflected from the location of the skin of the user is red or green.

3. The electronic device of claim 1, wherein the plurality of second blue-light emitting elements disposed in the second area emit a first amount of light in the biometric information measurement mode of the electronic device, wherein the first blue-light emitting elements disposed in the first area emit a second amount of light to display a blue component of an image in an image display mode of the electronic device, and wherein the first amount of light is greater than the second amount of light.

4. An electronic device comprising:
   a display panel including a first edge, a second edge, red-light emitting elements, green-light emitting elements, blue-light emitting elements, and light receiving elements that are spaced from each other, wherein the first edge and the second edge are opposite each other, wherein the blue-light emitting elements emit blue light in a biometric information measurement mode of the electronic device, wherein the light receiving elements receive reflected light in the biometric information measurement mode of the electronic device after the blue-light emitting elements have emitted the blue light, wherein the light receiving elements generate electrical signals in response to the reflected light, wherein the light receiving elements include a first light receiving element and a second light receiving element, wherein the first light receiving element is closer to the first edge than the second light receiving element is to the first edge, is farther from the first edge than the second light receiving element is from the second edge, and is farther from the second edge than the second light receiving element is from the second edge, wherein the first light receiving element neighbors one of first red-light emitting elements with no intervening first blue-light emitting elements between the first light receiving element and the one of the first red-light emitting elements, and wherein the second light receiving element neighbors two of second blue-light emitting elements with no intervening red-light emitting element or intervening green-light emitting element between the second light receiving element and either of the two of the second blue-light emitting elements; and
   a biometric information measurement module electrically connected to the display panel and configured to generate biometric information about a skin of the user based on the electrical signals,
   wherein the display panel comprises a display area including a first area and a second area, and a non-display area surrounding the display area,
   wherein the first area includes the first red-light emitting elements, first green-light emitting elements, the first blue-light emitting elements and the first light receiving element, and the second area includes a plurality of the second blue-light emitting elements and the second light receiving element,
   wherein the plurality of the second blue-light emitting elements includes a first-second blue-light emitting element, a second-second blue-light emitting element, a third-second blue-light emitting element and a fourth-second blue-light emitting element,
   wherein the second light receiving element is interposed between the first-second blue-light emitting element and the second-second blue-light emitting element along a first direction, and is interposed between the third-second blue-light emitting element and the fourth-second blue-light emitting element along a second direction perpendicular to the first direction, and wherein the second area does not include red-light emitting elements and green-light emitting elements.

5. The electronic device of claim 4, wherein the display panel further includes a base layer and a pixel defining layer, and wherein the pixel defining layer overlaps the base layer and includes openings that correspond to the red-light emitting elements, the green-light emitting elements, the blue-light emitting elements, and the light receiving elements.

6. The electronic device of claim 4, wherein the second light receiving element neighbors three of the second blue-light emitting elements with no intervening red-light emitting element or intervening green-light emitting element between the second light receiving element and any of the three of the second blue-light emitting elements.

7. The electronic device of claim 4, wherein the second light receiving element includes a first electrode, a second electrode, and a light receiving layer, wherein the light receiving layer is interposed between the first electrode and the second electrode and converts incident light into an electrical signal, and wherein the first electrode and the second electrode overlap each other.

8. The electronic device of claim 4, wherein the first light receiving element neighbors one of the first green-light emitting elements with no intervening first blue-light emitting element between the first light receiving element and the one of the first green-light emitting elements.

9. The electronic device of claim 4, wherein the second light receiving element neighbors four of the second blue-light emitting elements with no intervening red-light emitting element or intervening green-light emitting element between the second light receiving element and any of the four of the second blue-light emitting elements.

10. The electronic device of claim 9, wherein the second blue-light emitting elements disposed in the second area emit a first amount of light in a biometric information measurement mode of the electronic device, wherein the first blue-light emitting elements disposed in the first area emit a second amount of light in an image display mode of the electronic device, and wherein the first amount of light is greater than the second amount of light.

11. The electronic device of claim 4, wherein the light receiving elements generate the electrical signals in response to at least one of red light and green light in the reflected light.

12. The electronic device of claim 11, wherein the biometric information measurement module determines an inflammation state of a location of the skin of the user based on whether light reflected from the location of the skin of the user is red or green.

13. The electronic device of claim 4, wherein the biometric information measurement module generates the biometric information about the skin of the user based on at least one of a reflection location and a received amount of the reflected light.

14. The electronic device of claim 4, wherein the biometric information measurement module includes: a diagnosis part configured to determine inflammation information about the skin of the user based on the electrical signals.

15. The electronic device of claim 14, wherein the inflammation information includes inflammation location information and inflammation degree information, wherein the diagnosis part determines the inflammation location information based on a reflection location of the reflected light, and wherein the diagnosis part determines the inflammation degree information based on a received amount of the reflected light.

16. The electronic device of claim 4, wherein the second light receiving element is closer to the non-display area than the first light receiving element is to the non-display area.

17. A method for measuring biometric information, the method comprising:
emitting, using a display panel, blue light toward a skin of a user;
receiving, using the display panel, at least one of red light and green light reflected from the skin of the user; and
generating skin condition information of the user based on at least one of a reflection location and a received amount of the at least one of the red light and the green light,
wherein the display panel comprises a display area including a first area and a second area, and a non-display area surrounding the display area,
wherein the first area includes first red-light emitting elements, first green-light emitting elements, first blue-light emitting elements and a first light receiving element, and the second area includes a plurality of second blue-light emitting elements and a second light receiving element,
wherein the plurality of the second blue-light emitting elements includes a first-second blue-light emitting element, a second-second blue-light emitting element, a third-second blue-light emitting element and a fourth-second blue-light emitting element,
wherein the second light receiving element is interposed between the first-second blue-light emitting element and the second-second blue-light emitting element along a first direction, and is interposed between the third-second blue-light emitting element and the fourth-second blue-light emitting element along a second direction perpendicular to the first direction, and
wherein the second area does not include red-light emitting elements and green-light emitting elements.

18. The method of claim 17, wherein the display panel emits a first amount of blue light when the user does not directly look at a display area of the display panel, wherein the display panel emits a second amount of blue light when the user directly looks at an image displayed in the display area of the display panel, and wherein the first amount of blue light is greater than the second amount of blue light.

19. The method of claim 17, wherein the display panel includes more blue-light emitting elements than red-light emitting elements or green-light emitting elements.

20. The method of claim 17, wherein the display panel includes a first edge, and a second edge, wherein the first edge and the second edge are opposite each other, wherein the first light receiving element is closer to the first edge than the second light receiving element is to the first edge, is farther from the first edge than the second light receiving element is from the second edge, and is farther from the second edge than the second light receiving element is from the second edge, wherein the first light receiving element neighbors one of the first red-light emitting elements with no intervening first blue-light emitting elements between the first light receiving element and the one of the first red-light emitting elements, and wherein the second light receiving element neighbors two of the second blue-light emitting elements with no intervening red-light emitting element or intervening green-light emitting element between the second light receiving element and either of the two of the second blue-light emitting elements.

21. The method of claim 17, wherein the display panel receives the red light reflected from a first inflammation of the skin of the user, and wherein the display panel receives the green light reflected from a second inflammation of the skin of the user.

22. The method of claim 21, further comprising: displaying, using the display panel, the skin condition information of the user to the user, wherein the skin condition information of the user includes at least one of a location and a degree of each of the first inflammation and the second inflammation.

23. The method of claim 22, further comprising:
   determining, using a module electrically connected to the display panel, a prescription based on the skin condition information of the user.

* * * * *